(12) United States Patent
Amitani et al.

(10) Patent No.: US 7,979,287 B2
(45) Date of Patent: Jul. 12, 2011

(54) RADIATION IMAGE RADIOGRAPHING SYSTEM, CONTROL APPARATUS, RADIATION IMAGE DETECTING APPARATUS AND MANAGEMENT APPARATUS

(75) Inventors: Kouji Amitani, Tachikawa (JP); Mamoru Umeki, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 779 days.

(21) Appl. No.: 11/960,416

(22) Filed: Dec. 19, 2007

(65) Prior Publication Data
US 2008/0154744 A1   Jun. 26, 2008

(30) Foreign Application Priority Data

Dec. 22, 2006 (JP) .............................. JP2006-345536
Dec. 22, 2006 (JP) .............................. JP2006-345537
Feb. 7, 2007 (JP) .............................. JP2007-027824

(51) Int. Cl.
*G06Q 50/00* (2006.01)
*G06Q 10/00* (2006.01)

(52) U.S. Cl. .......................................... 705/2; 378/197

(58) Field of Classification Search ................. 705/2–3; 378/197
See application file for complete search history.

(56) References Cited

U.S. PATENT DOCUMENTS

2004/0240624 A1 * 12/2004 Shiibashi et al. ............. 378/197
2005/0215867 A1   9/2005 Grigsby et al.

FOREIGN PATENT DOCUMENTS

| EP | 1 420 354 | 5/2004 |
| EP | 1 462 055 | 9/2004 |
| JP | 2006-198043 | 8/2006 |

OTHER PUBLICATIONS

European Search Report dated Jun. 16, 2008.

* cited by examiner

*Primary Examiner* — Luke Gilligan
(74) *Attorney, Agent, or Firm* — Finnegan, Henderson, Farabow, Garrett & Dunner, L.L.P.

(57) ABSTRACT

The console selects one radiographing order information item from the radiographing order information list stored in the storing section. A step is taken to determine whether or not the one selected radiographing order information item has a predetermined relationship with the other radiographing order information, and the permission of additional selection is granted only to the radiographing order information having a predetermined relationship.

18 Claims, 16 Drawing Sheets

FIG. 5

| RADIOGRAPHING ORDER ID | PATIENT ID | PATIENT NAME | SEX | AGE | WARD | DIAGNOSIS DEPARTMENT | RADIOGRAPHING REGION | RADIOGRAPHING DIRECTION |
|---|---|---|---|---|---|---|---|---|
| 001 | 100085 | ICHIRO SUZUKI | MALE | 25 | 101 | SURGERY | CHEST | FRONT A-P |
| 002 | 100085 | ICHIRO SUZUKI | MALE | 25 | 101 | SURGERY | CHEST | SIDE L |
| 003 | 100085 | ICHIRO SUZUKI | MALE | 25 | 101 | SURGERY | CHEST | SIDE R |
| 004 | 100125 | RIN YAGUCHI | FEMALE | 55 | 305 | GYNECOLOGY | BREAST | MLO-R |
| 005 | 100125 | RIN YAGUCHI | FEMALE | 55 | 305 | GYNECOLOGY | BREAST | MLO-L |
| 006 | 100125 | RIN YAGUCHI | FEMALE | 55 | 305 | GYNECOLOGY | BREAST | CC-L |
| 007 | 100125 | RIN YAGUCHI | FEMALE | 55 | 305 | GYNECOLOGY | BREAST | CC-R |
| 008 | 100320 | JIRO SATO | MALE | 15 | 410 | ORTHOPEDICS | LEG | L |
| 009 | 100325 | EISAKU YOSHIDA | MALE | 60 | 115 | ORTHOPEDICS | HAND | L |

| RADIOGRAPHING ORDER ID | PATIENT ID | PATIENT NAME | SEX | AGE | WARD | DIAGNOSIS DEPARTMENT | RADIOGRAPHING REGION | RADIOGRAPHING DIRECTION |
|---|---|---|---|---|---|---|---|---|
| 001 | 100085 | ICHIRO SUZUKI | MALE | 25 | 101 | SURGERY | CHEST | FRONT A-P |
| 002 | 100085 | ICHIRO SUZUKI | MALE | 25 | 101 | SURGERY | CHEST | SIDE L |
| 003 | 100085 | ICHIRO SUZUKI | MALE | 25 | 101 | SURGERY | CHEST | SIDE R |
| 004 | 100125 | RIN YAGUCHI | FEMALE | 55 | 305 | GYNECOLOGY | BREAST | MLO-R |
| 005 | 100125 | RIN YAGUCHI | FEMALE | 55 | 305 | GYNECOLOGY | BREAST | MLO-L |
| 006 | 100125 | RIN YAGUCHI | FEMALE | 55 | 305 | GYNECOLOGY | BREAST | CC-L |
| 007 | 100125 | RIN YAGUCHI | FEMALE | 55 | 305 | GYNECOLOGY | BREAST | CC-R |
| 008 | 100320 | JIRO SATO | MALE | 15 | 410 | ORTHOPEDICS | LEG | L |

PLEASE INPUT RADIOGRAPHING ORDER INFORMATION

DETERMINE
RETURN

FIG. 7

SELECTED RADIOGRAPHING ORDER INFORMATION

| RADIOGRAPHING ORDER ID | PATIENT ID | PATIENT NAME | SEX | AGE | WARD | DIAGNOSIS DEPARTMENT | RADIOGRAPHING REGION | RADIOGRAPHING DIRECTION |
|---|---|---|---|---|---|---|---|---|
| 001 | 100085 | ICHIRO SUZUKI | MALE | 25 | 101 | SURGERY | CHEST | FRONT A-P |

PLEASE INPUT RADIOGRAPHING ORDER INFORMATION

| RADIOGRAPHING ORDER ID | PATIENT ID | PATIENT NAME | SEX | AGE | WARD | DIAGNOSIS DEPARTMENT | RADIOGRAPHING REGION | RADIOGRAPHING DIRECTION |
|---|---|---|---|---|---|---|---|---|
| 002 | 100085 | ICHIRO SUZUKI | MALE | 25 | 101 | SURGERY | CHEST | SIDE L |
| 003 | 100085 | ICHIRO SUZUKI | MALE | 25 | 101 | SURGERY | CHEST | SIDE R |

(RETURN) (DETERMINE)

FIG. 8

PLEASE INPUT RADIOGRAPHING MODE (CR MODE) (FPD MODE)

(RETURN) (DETERMINE)

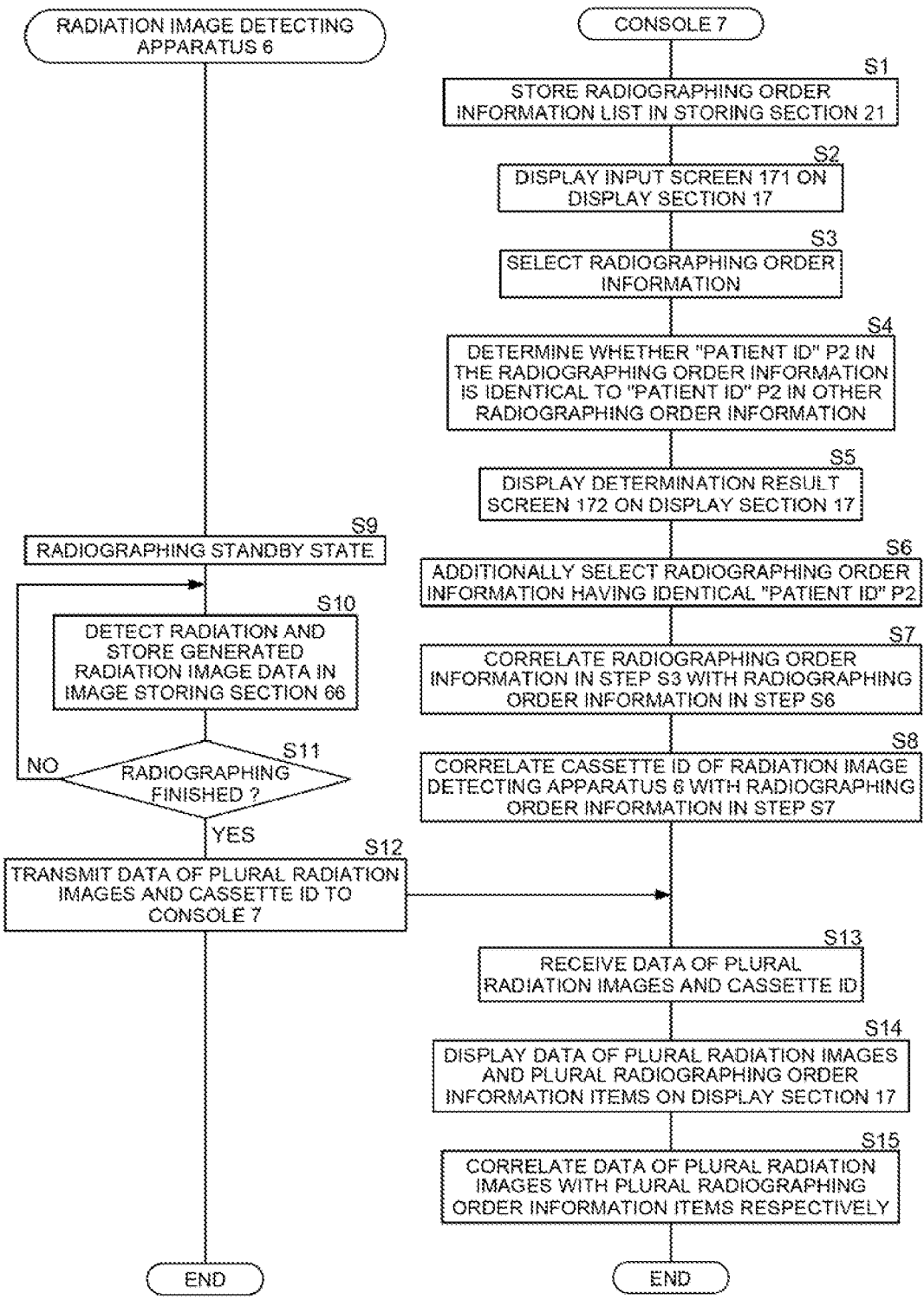

RADIATION IMAGE RADIOGRAPHING SYSTEM, CONTROL APPARATUS, RADIATION IMAGE DETECTING APPARATUS AND MANAGEMENT APPARATUS

This application is based on Japanese Patent Application Nos. 2006-345536 filed on Dec. 22, 2006, 2006-345537 filed on Dec. 22, 2006 and 2007-027824 filed on Feb. 7, 2007 in Japanese Patent Office, the entire content of which is hereby incorporated by reference.

BACKGROUND OF THE INVENTION

The present invention relates to a radiation image detecting apparatus for generating radiation image data by detecting radiation represented by X-rays, a control apparatus for controlling this radiation image detecting apparatus, a plurality of control apparatuses for receiving radiation image data generated by detecting a radiation by the radiation image detecting apparatus, a management apparatus for managing the plurality of control apparatuses, and a radiation image radiographing system using the radiation image detecting apparatus, control apparatus or management apparatus, and mobile information terminal apparatus.

In the field of medical diagnosis, a CR (Computed Radiography) system capable of handling a radiation image as digital data is put into commercial use. This CR system is made up of a reading apparatus for reading radiation image data by scanning the phosphor plate incorporated in the CR cassette through excitation light, and a control apparatus (also referred to as a console) for obtaining radiation image data read by this reading apparatus, wherein these two component apparatuses are connected with each other. The CR cassette exposed to radiation in a radiographing room is read by the reading apparatus, and the obtained radiation image data is transmitted to the control apparatus and is displayed, whereby the radiographing technician is allowed to make sure whether the optimum radiation image data has been obtained or not.

A large-scale CR system wherein a plurality of reading apparatuses and a plurality of control apparatuses are connected over the network has been proposed in recent years for use in a medical institution equipped with a plurality of radiographing rooms (Patent Document 1). In the large-scale CR system as described in this Patent Document 1, there are a plurality of patients to be radiographed at one time, and a plurality of radiographing technicians in charge of radiographing operation. This may cause confusion of radiation image data among different patients. To prevent this confusion, the instruction information known under the name of radiographing order information incorporating the patient information (e.g., patient name and age) and radiographing information (e.g., radiographing date, radiographing region and radiographing direction) is prepared in advance, and this radiographing order information is correlated with the cassette ID (identification information) for identification of CR cassette, whereby this information is registered. Thus, if one piece of radiographing order information is correlated with one CR cassette, the radiation image data obtained by reading the CR cassette with the reading apparatus is correlated with the radiographing order information based on the cassette ID of the CR cassette, whereby confusion of radiation image data can be prevented.

To permit radiographing of a patient who cannot be moved to the X-ray room due to serious cases and others, a traveling type irradiation apparatus for a doctor's round has been implemented. As a method having been proposed (e.g., Patent Document 2), effective radiographing operation at the site of visit can be ensured by carrying a mobile information terminal apparatus (PDA (Personal Digital Assistance)), together with this irradiation apparatus for a doctor's round. Generally, in the method of radiographing by a doctor making a round with the PDA, the radiographing order information for planned radiographing at the site visited by the doctor is transmitted from a control apparatus to the PDA so that this radiographing order information is stored in the PDA. After that, this PDA, the irradiation apparatus for doctor's round and the CR cassettes in the number corresponding to the number of radiographing operations are carried to the site visited by the doctor. At the site visited by the doctor, radiographing order information for radiographing operation is displayed on the PDA, and the CR cassette barcode (cassette ID) is read by the barcode reader mounted on the PDA, whereby correlation is established between the displayed radiographing order information and the cassette ID. After that, according to the radiographing order information, the irradiation apparatus for doctor's rounds is operated so that the radiation images are stored in the CR cassette. This CR cassette is read by the reading apparatus and the radiation image data having been obtained is transmitted to the control apparatus. Further, the correlation between the radiographing order information and cassette ID stored in the PDA is transmitted to the control apparatus wherein the correlation is established between the radiographing order information and radiation image data. As described above, if the PDA is brought to the site visited by the doctor, the radiographing order information is verified at the site visited by the doctor. After that, correlation is established between this radiographing order information and CR cassette for performing the radiographing. This arrangement eliminates the possibility of radiation image data being confused.

A proposal has been made of an FPD (Flat Panel Detector) apparatus as a radiation image detecting apparatus wherein this FPD apparatus incorporates the radiation detecting elements in a two-dimensional array on the substrate instead of the aforementioned CR cassette, and is capable of outputting the electric signal in response to the radiation dose applied to this radiation detecting element (e.g., Patent Document 3). Use of this FPD apparatus eliminates the need of using a reading apparatus that reads the radiation image by exposure to the excitation light, and directly gets the radiation image. This arrangement simplifies the system as compared to the case of using the CR cassette. This ensures more effective radiographing operation. Further, data of plural radiation images can be stored by the storing section incorporated in the FPD apparatus, and plural radiographing operations can be performed continuously in one time, with the result that radiographing efficiency is enhanced.

Because of such conveniences of the FPD apparatus, the FPD apparatus is anticipated to be applied to also the aforementioned large-scale CR system in future, as described in the Patent Document 2. Particularly in the radiographing by a doctor making a round, a plurality of radiographing operations are commonly performed in one round, use of an FPD apparatus eliminates the need of carrying the cassettes in the number corresponding to several radiographing operations to the site visited by the doctor, with the result that easy and convenient radiographing operations can be performed.

However, although the FPD apparatus offers an advantage of storing data of plural radiation images in one operation, it involves a higher possibility of causing an error in the correlation between the radiographing order information and radiation image data, and diagnosis may be carried out without the doctor becoming conscious of this error. To be more specific, if data of plural radiation images is stored in one FPD apparatus, even if plural radiographing order information for data of plural radiation images and the identification information of the FPD apparatus are registered correlated with each other in advance, the incorrect correlation will be established between radiation image data and radiographing order information when the order of performing radiographing operations have been replaced.

Further, in the radiographing operation by a doctor making a round of visits using the aforementioned PDA, if the FPD apparatus is used instead of CR cassette, incorrect correlation may be established between the radiographing order information and radiation image data. Further, diagnosis may be carried out without the doctor becoming conscious of this error.

For example, when radiographing operations are performed using one FDA apparatus in one radiographing operation during doctor's round, plural radiographing order information for the planned radiographing operation is stored in the PDA, and the correlation is established between the plural radiographing order information stored in the PDA and one FPD apparatus. Then radiographing operation is performed according to the order number included in radiographing order information, starting with the lowest numbers. Thus, radiation image data corresponding to plural radiographing operations is stored in one FPD apparatus. Data of plural radiation images stored in the FPD apparatus, and information about correlation between radiographing order information stored in the PDA and FPD apparatus are transmitted to the control apparatus. After that, correlation is established between the radiographing order information and radiation image data by the control apparatus based on the order number and radiographing sequential order.

However, for example, if the order of radiographing operations is replaced to suit the convenience of a patient or doctor, incorrect correlation will be established between radiation image data and radiographing order information in the control apparatus. In this case, if the plural radiation image data is of a plurality of patients wherein the radiographing regions are identical to each other (or similar to each other), radiation image data cannot be identified and it is difficult to find an error in correlation. This makes it difficult to establish correct correlation between the radiation image data and radiographing order information, and will hence lead to a serious medical error.

[Patent Document 1] Unexamined Japanese Patent Application Publication No. 2002-159476

[Patent Document 2] Unexamined Japanese Patent Application Publication No. 2004-147910

[Patent Document 3] Unexamined Japanese Patent Application Publication No. 2006-122304

SUMMARY

An object of the present invention is to solve the aforementioned problems and to provide an radiation image radiographing system which ensures correct correlation between the radiographing order information and radiation image data, even if an FPD apparatus is used as a radiation image detecting apparatus, as well as the radiation image detecting apparatus thereof and control apparatus and management apparatus thereof.

To achieve the aforementioned object, the radiation image radiographing system of the present invention includes:

a control apparatus for storing plural radiographing order information on radiographing; and a radiation image detecting apparatus which, when radiographing operation is performed based on at least two radiographing order information items selected from among the aforementioned plural radiographing order information items, can generate and store radiation image data corresponding to the aforementioned two or more radiographing order information items with these apparatuses being connected communicably in the aforementioned radiation image radiographing system;

wherein this radiation image radiographing system of the present invention further includes;

a selection device which, in the selection of the aforementioned two or more radiographing order information items, selects at least one radiographing order information item out of plural radiographing order information items stored in the aforementioned control apparatus;

a determining device that determines whether or not there is a predetermined relationship between the one radiographing order information item selected by this selection device, and the other radiographing order information item different from this radiographing order information; and a permission device for granting permission of additional selection only to the other radiographing order information item determined as having a predetermined relationship by this determining device.

To achieve the aforementioned object, the control apparatus of the present invention is connected communicably with a radiation image detecting apparatus which, when radiographing operation is performed based on at least two radiographing order information items selected from among the plural radiographing order information items, can generate and store radiation image data corresponding to the aforementioned two or more radiographing order information items;

wherein this the control apparatus contains:

a control storing section for storing the aforementioned plural radiographing order information items;

a selection device which, in the selection of the aforementioned two or more radiographing order information items, selects at least one radiographing order information item out of plural radiographing order information items stored in the aforementioned control storing apparatus;

a determining device that determines whether or not there is a predetermined relationship between the one radiographing order information item selected by this selection device, and the other radiographing order information item different from this radiographing order information; and a permission device for granting permission of additional selection only to the other radiographing order information item determined as having a predetermined relationship by this determining device.

To achieve the aforementioned object, the radiation image detecting apparatus of this invention is connected communicably with the control apparatus for storing plural radiographing order information items, wherein this radiation image detecting apparatus includes;

a receiving section for receiving at least two radiographing order information items out of the aforementioned plural radiographing order information items;

a radiographing order information storing section for storing one radiographing order information item received by the aforementioned receiving section, as the radiographing order information having been selected;

a determining device that determines whether or not there is a predetermined relationship between the selected radiographing order information item stored in the aforementioned radiographing order information storing section, and the other radiographing order information item different from this selected radiographing order information;

a permission device for granting permission of additional selection only to the other radiographing order information item determined as having a predetermined relationship by this determining device;

an image data generating section which, by detecting the radiation having passed through a subject, generates radiation image data corresponding to each of the aforementioned selected radiographing order information and the other radiographing order information granted permission of additional selection by the aforementioned permission device; and an image storing section for storing data of plural radiation images generated by the aforementioned image data generating section.

To achieve the aforementioned object, the radiation image radiographing system of the present invention includes:

an radiation image detecting apparatus for generating radiation image data by detecting the radiation having passed through a subject, a control apparatus for selecting the radiographing order information on radiographing operation; and a management apparatus for transmitting to the aforementioned radiation image detecting apparatus, the two or more radiographing order information items including the radiographing order information selected by this control apparatus with these apparatuses being connected communicably in the radiation image radiographing system;

wherein this radiation image radiographing system, when radiographing operation is performed based on at least two radiographing order information items transmitted from the aforementioned management apparatus, can generate and store the radiation image data corresponding to the aforementioned two or more radiographing order information by the aforementioned radiation image detecting apparatus;

wherein the aforementioned control apparatus includes:

a selection device which, when selecting the aforementioned two or more radiographing order information items, selects at least one radiographing order information item out of plural radiographing order information items; and a first transmitting section for transmitting to the aforementioned management apparatus, one radiographing order information item selected by this selection device;

wherein the aforementioned management apparatus includes;

a receiving section for receiving one radiographing order information item transmitted from the aforementioned first transmitting section;

a determining device that determines whether or not there is a predetermined relationship between the one radiographing order information item received by the receiving section, and the other radiographing order information item different therefrom;

a permission device for granting permission of additional selection only to the other radiographing order information item determined as having a predetermined relationship by this determining device; and a second transmitting section for transmitting to the aforementioned radiation image detecting apparatus, the aforementioned one radiographing order information item and the other radiographing order information item granted permission of additional selection by the aforementioned permission device.

To achieve the aforementioned object, the management apparatus of the present invention connected communicably with:

a control apparatus for selecting at least one radiographing order information item for radiographing operation; and a radiation image detecting apparatus for receiving at least two radiographing order information items including the aforementioned one radiographing order information, and capable of generating and storing the radiation image data corresponding to the two or more radiographing order information;

wherein the aforementioned management apparatus includes:

a receiving section which, when selecting the aforementioned two or more radiographing order information items, receives the one radiographing order information item selected by the aforementioned control apparatus;

a determining device that determines whether or not there is a predetermined relationship between the one radiographing order information item received by the aforementioned receiving section, and the other radiographing order information item different from the one radiographing order information;

a permission device for granting permission of additional selection only to the other radiographing order information item determined as having a predetermined relationship by this determining device; and a radiographing order information transmitting section for transmitting to the aforementioned radiation image detecting apparatus, the aforementioned one radiographing order information and the other radiographing order information item granted the permission of additional selection by the aforementioned permission device.

To achieve the aforementioned object, the radiation image radiographing system of the present invention includes;

a control apparatus for storing plural radiographing order information for radiographing operation;

a mobile information terminal apparatus for storing at least two radiographing order information items selected from among the aforementioned plural radiographing order information items; and a radiation image detecting apparatus capable of generating and storing the radiation image data corresponding to the aforementioned two or more radiographing order information items with these apparatuses being connected communicably in the aforementioned radiation image radiographing system;

wherein the aforementioned radiation image radiographing system further includes;

a radiographing order information selection device which, in the selection of the aforementioned two or more radiographing order information items, selects at least one radiographing order information item out of plural radiographing order information items stored in the aforementioned control apparatus; and a determining device that determines whether or not there is a predetermined relationship between the one radiographing order information item selected by this radiographing order information selection device, and the other radiographing order information item different from this radiographing order information.

To achieve the aforementioned object, the control apparatus of the present invention is communicably connected with a mobile information terminal apparatus for storing at least two radiographing order information items selected out of plural radiographing order information items, wherein the aforementioned control apparatus includes;

a storing section for storing the aforementioned plural radiographing order information items;

a radiographing order information selection device which, in the selection of the aforementioned two or more radiographing order information items, selects at least one radiographing order information item out of plural radiographing order information items stored in the aforementioned storing section;

a determining device that determines whether or not there is a predetermined relationship between the one radiographing order information item selected by this radiographing order information selection device, and the other radiographing order information item different from this radiographing order information; and a transmitting section for transmitting to the aforementioned mobile information terminal apparatus, the one radiographing order information item selected by the aforementioned radiographing order information selection device and at least one radiographing order information item selected from among other radiographing order information items determined as having a predetermined relationship by the aforementioned determining device.

BRIEF DESCRIPTION OF THE DRAWINGS

FIG. 5 is a diagram representing an example of the radiographing order information list;

FIG. 6 is an example showing that the input screen for inputting the radiographing order information is indicated on a display section;

FIG. 7 is an example showing that the determination result screen representing the result of determination step is displayed on a display section;

FIG. 8 is an example showing that the radiographing mode input screen for inputting the radiographing mode is displayed on a display section;

FIG. 9 is a flow chart representing the operation of the radiation image radiographing system as a first embodiment;

DETAILED DESCRIPTION OF THE PREFERRED EMBODIMENT

The following describes the embodiment of the present invention with reference to drawings, without the technological scope of the present invention being restricted by the description of the present embodiment.

Figure 1:
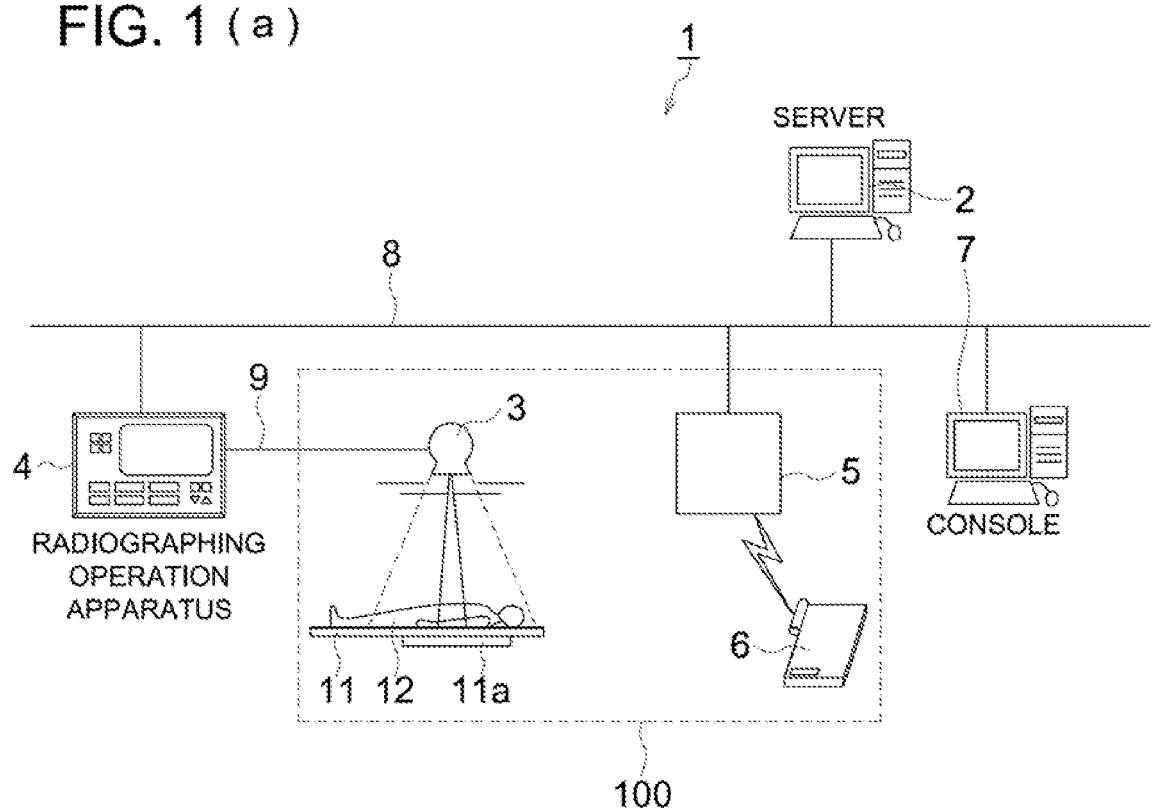
FIG. 1(a) is a schematic diagram showing first through third embodiments in the RIS of the present invention.
FIG. 1(b) is a schematic diagram showing a fourth embodiment in the RIS of the present invention.

FIG. 1(a) is a schematic diagram showing first through third embodiments in the RIS (Radiography Information System) of the present invention.

The RIS 1 for managing the information on radiographic diagnosis and treatment according to the present embodiment includes:

an RIS server 2 for managing the information on radiographing, as shown in 1 (1); a radiographing operation apparatus 4 for performing radiographing operation; a base station 5 for wireless communications, for example, on a wireless LAN (Local Area Network); a console 7 for applying imaging processing to the radiation image data generated by the radiation image detecting apparatus 6; and these devices are connected over the network 8. A console 7 and a radiation image detecting apparatus 6 constitute a radiation image radiographing system 200. Although not illustrated, the RIS 1 is connected with the HIS (Hospital Information System) for centralized management of the patient diagnosis information and accounting information, over the network 8. The network 8 can be a communications line devoted solely to this system, which may reduce the degree of freedom in the system configuration. Accordingly, use of an existing line such as the Ethernet (registered trademark) is recommended.

The radiographing operation apparatus 4 is connected through the cable 9 with a radiation image radiographing apparatus 3 for radiographing a subject by applying radiation. The radiation image radiographing apparatus 3, base station 5 and others are arranged in a radiographing room 100. It is also possible to make such arrangements that the radiographing operation apparatus 4 is installed in the radiographing room 100. Although not illustrated, a plurality of the apparatuses other than the RIS server 2 are installed and connected in conformity to the size and configuration of the facility where the RIS 1 is installed. Thus, a plurality of radiographing operations can be performed across a plurality of radiographing rooms 100 by one radiation image detecting apparatus 6.

At the time of wireless communication between the server 2 and radiation image detecting apparatus 6, or the radiation image detecting apparatus 6 and console 7, the base station 5 has a function of relaying these communications.

<Server>

Figure 2:
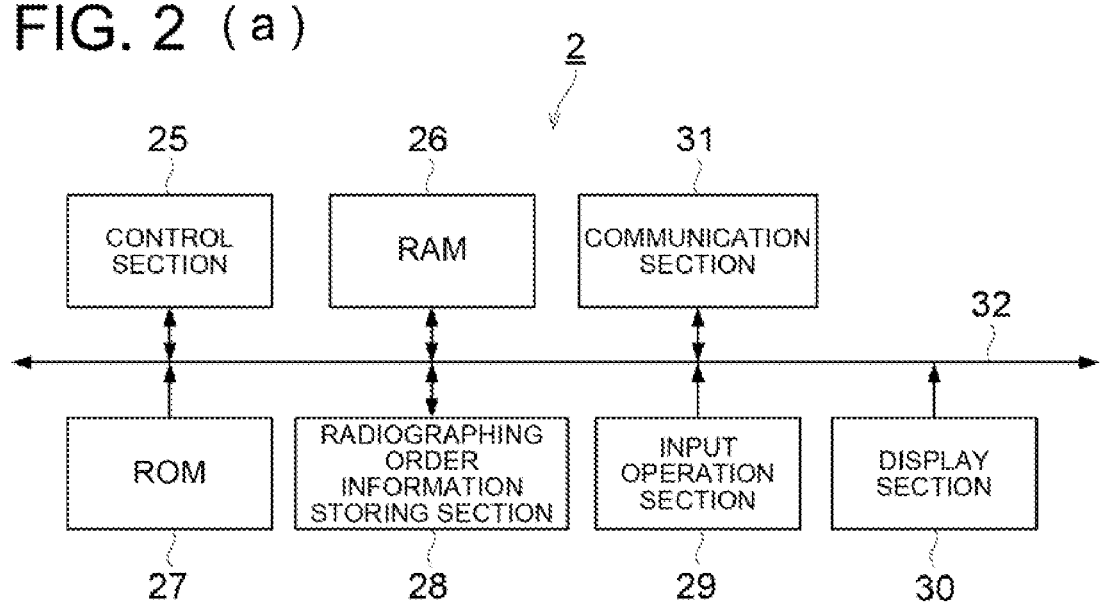
FIG. 2(a) is a block diagram representing the major components of a server.
FIG. 2(b) is a block diagram representing the major components of a console.
FIG. 2(c) is a block diagram representing the major components of a radiation image detecting apparatus.
FIG. 2(d) is a block diagram representing the major components of a PDA.
Figure 2:
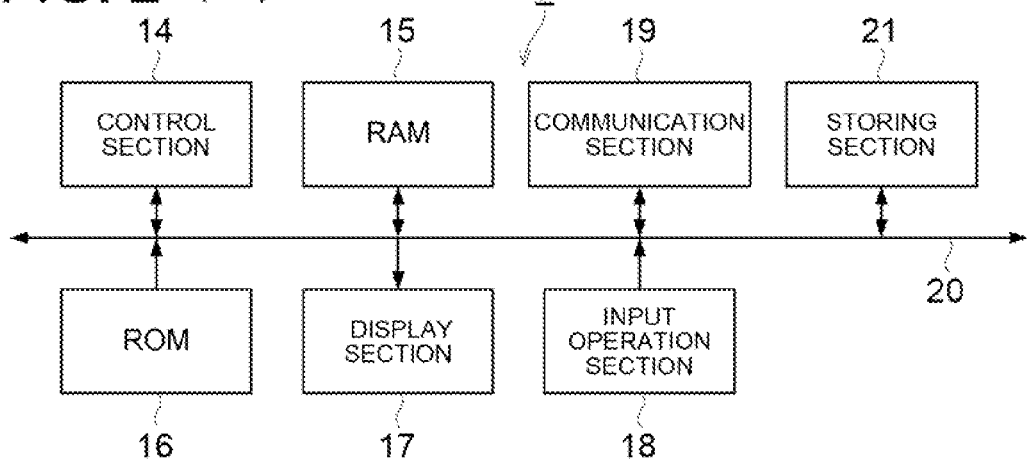
Figure 2:
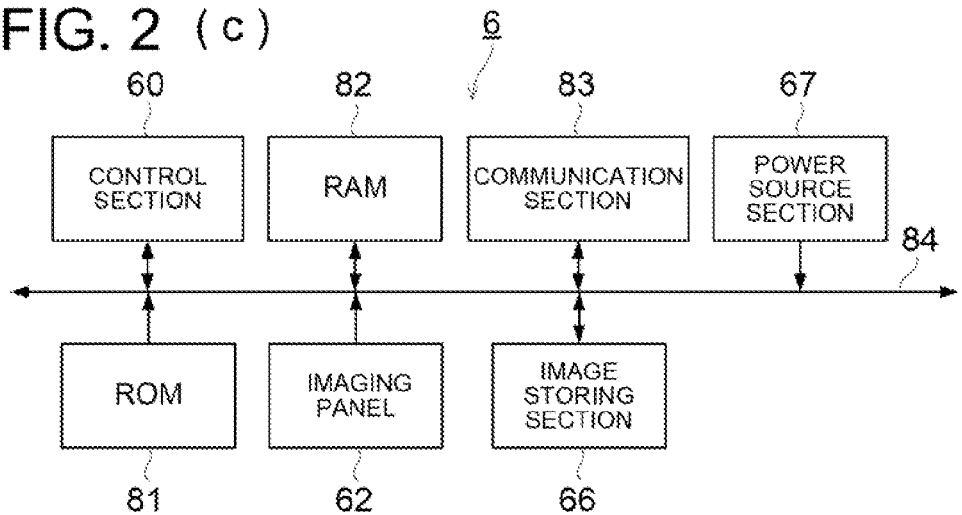
Figure 2:
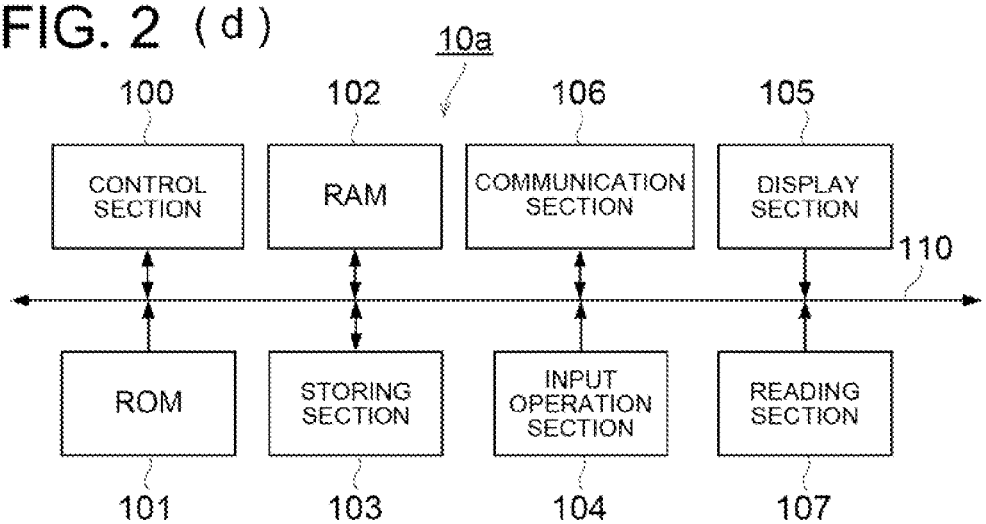

FIG. 2(a) is a block diagram representing the major components of a server 2.

The server 2 as a management apparatus is constructed of a computer equipped with a control section 25, RAM 26, ROM 27, radiographing order information storing section 28, input operation section 29, display section 30, communication section 31 and others, as illustrated. These components are connected by a bus 32.

The ROM (Read Only Memory) 27 is made up of a nonvolatile semiconductor memory or others, and stores the control program to be executed by the control section 25.

The RAM (Random Access Memory) 26 forms a work area for temporarily storing various forms of programs that can be read out from ROM 27 and executed by the control section 25, input or output data, parameters and others, in various forms of processing to be implemented and controlled by the control section 25.

The radiographing order information storing section 28 stores plural radiographing order information items wherein the patient information and radiographing information are generated in the correlated form.

FIG. 5 is a diagram representing an example of the radiographing order information list made up of plural radiographing order information items. As shown in FIG. 5, the radiographing order information includes such patient information as "patient ID" P2, "patient name" P3, "sex" P4, "age" P5, "ward" P6 and such radiographing information as "diagnosis department" P7, "radiographing region" P8, and "radiographing direction" P9. In the order of receiving the radiographing order, the "radiographing order ID" P1 is automatically assigned to each of the radiographing order information items. The patient information and radiographing information are not restricted to the aforementioned ones. For example, such information as the birth of date of the patient, the number of medical examinations and radiation dose can be included. All of these information items need not be included. The information contained in the radiographing order information can be set in conformity to the purpose of radiographing and radiographing flow.

The input operation section 29 is constructed of a keyboard, mouse and others. The depression signal or the key depressed on the keyboard and the mouse operation signal are outputted to the control section 29 as input signals. To put it more specifically, the aforementioned patient information and radiographing information can be inputted, or various forms of setting information of the server 2 can be inputted.

The display section 30 is provided with a CRT (Cathode Ray Tube), LCD (Liquid Crystal Display) and others. In response to the instruction of the display signal outputted or inputted from the control section 25, various types of screens such as the input screen of the radiographing order information and others are displayed.

The communication section 31 as a radiographing order information transmitting section, the second transmitting section and receiving section is an interface for exchange of various forms of information with a plurality of consoles 7, and is connected with the network 8 according to the standards such as the USB (Universal Serial Bus) and IEEE (Institute of Electrical and Electronic Engineers) 1394. Further, the communication section 31 performs wireless communication of various types of information with the radiation image detecting apparatus 6 on a wireless LAN conforming to the IEEE 802.11 Standard through the base station 5 connected to the network 8. In addition to the wireless communication using the electric wave (space wave), the wireless communication includes the optical wireless communication using the infrared ray and visible light (such as a laser) and acoustic communication using the sound wave or ultrasonic wave.

The control section 25 is made of the CPU (Central Processing Unit), for example. It reads a predetermined program stored in the ROM 16 and loads it in the work area of the RAM 15. Then it applies various forms of processing according to the program. For example, the control section 25 correlates the patient information inputted from the input operation section 29 and the radiographing information with each other, and generates radiographing order information, whereby the generated plural radiographing order information items are stored in the radiographing order information storing section 28. Further, the control section 25 makes a comparison between one radiographing order information item transmitted from the console 7 and the other radiographing order information item stored in the radiographing order information storing section 28 so that a decision is made to see whether or not the other radiographing order information item is in a predetermined relationship with the one radiographing order information item. In other words, this control section 25 corresponds to the determining device of the present embodiment.

The radiation image radiographing apparatus 3 applies radiation to the patient 12 as a subject lying on the radiographic stand 11 for lying position. A detecting apparatus mounting port 11a for mounting the radiation image detecting apparatus 6 is installed below the radiographic stand 11 for lying position. The radiation image radiographing apparatus 3 is controlled by the radiographing operation apparatus 4, whereby radiographing is performed under predetermined radiographing conditions.

<Console>

FIG. 2(b) is a block diagram representing the major components of the console 7.

As shown in FIG. 2(b), the console 7 as a control apparatus is basically designed in almost the same hardware structure as that of the server 2. It is made of a computer equipped with a control section 14, RAM 15, ROM 16, display section 17, input operation section 18, communication section 19, and storing section 21. These components are connected by a bus 20.

The ROM (Read Only Memory) 16 is composed of a nonvolatile semiconducting memory and others, and stores the control program to be run by the control section 14, and image processing conditions.

In various forms of processing applied under the control of the control section 14, the RAM (Random Access Memory) 15 forms a work area for temporarily storing the various forms of programs that can be read out from the ROM 16 and can be executed by the control section 14, inputted or outputted data, parameters and others.

The display section 17 is provided with a CRT (Cathode Ray Tube) and LCD (Liquid Crystal Display), for example. In response to the instruction of the display signal outputted or inputted from the control section 14, various types of screens are displayed. For example, the display section 17 displays plural radiographing order information items received through the communication section 19 to be described later.

The input operation section 18 is made of a keyboard and mouse, for example.

The depression signal of the key depressed on the keyboard and the mouse operation signal are outputted to the control section 14 as input signals. To put it more specifically, it is possible to input the cassette ID as identification information assigned to the radiation image detecting apparatus 6, or the one radiographing order information item out of plural radiographing order information items displayed on the display section 17. It is also possible to use a barcode reader as the input operation section 18 and to read the barcode assigned to the radiation image detecting apparatus 6, thereby inputting the cassette ID of the radiation image detecting apparatus 6.

The communication section 13 is used to perform wireless communication of various forms of information with the radiation image detecting apparatus 6 through the base station 5 on the wireless LAN conforming to the IEEE (Institute of Electrical and Electronic Engineers) 802.11 Standard. In addition to the wireless communication using the electric wave (space wave), the wireless communication includes the optical wireless communication using the infrared ray and visible light (such as laser) and acoustic communication using the sound wave or ultrasonic wave. It is also possible to receive various forms of information from the RIS server 2 over the network 8.

The control section 14 is made of the CPU (Central Processing Unit) and others, for example. It reads a predetermined program stored in the ROM 16 and loads it in the work area of the RAM 15. Then it applies various forms of processing according to the program. In collaboration with the communication section 19, this control section 14 receives the radiographing order information list stored in the external storing apparatus of the RIS server 2 over the network 8. Further, the control section 14 receives the radiation image data from the radiation image detecting apparatus 6 through the base station 5 by wireless communication. The control section 14 also applies image processing such as normalization and gradation processing to the radiation image data, based on the image processing conditions stored in the ROM 16. Further, receiving the input from the input operation section 18, the control section 14 selects one radiographing order information item from among plural radiographing order information items stored in the storing section 21 (to be described later). It also determines whether or not there is a predetermined relationship between the aforementioned one radiographing order information item and the other radiographing order information stored in the storing section 21. In other words, this control section 14 corresponds to the selection device and determining device of the present embodiment.

The storing section 21 stores the radiographing order information list received, from the RIS server 2 through the communication section 19, and the radiation image data transmitted from the radiation image detecting apparatus 6. The storing section 21 correlates the radiographing order information with radiation image data and stores them. In other words, the storing section 21 corresponds to the control storing section of the present embodiment.

<Radiation Image Detecting Apparatus>

The radiation image detecting apparatus 6 obtains the radiation image data by detecting the radiation which has been emitted from the radiation image radiographing apparatus 3 and has passed through the patient 12. It is a portable cassette type FPD apparatus made up of a cassette incorporating an imaging panel which is called Flat Panel Detector (FPD).

Figure 3:
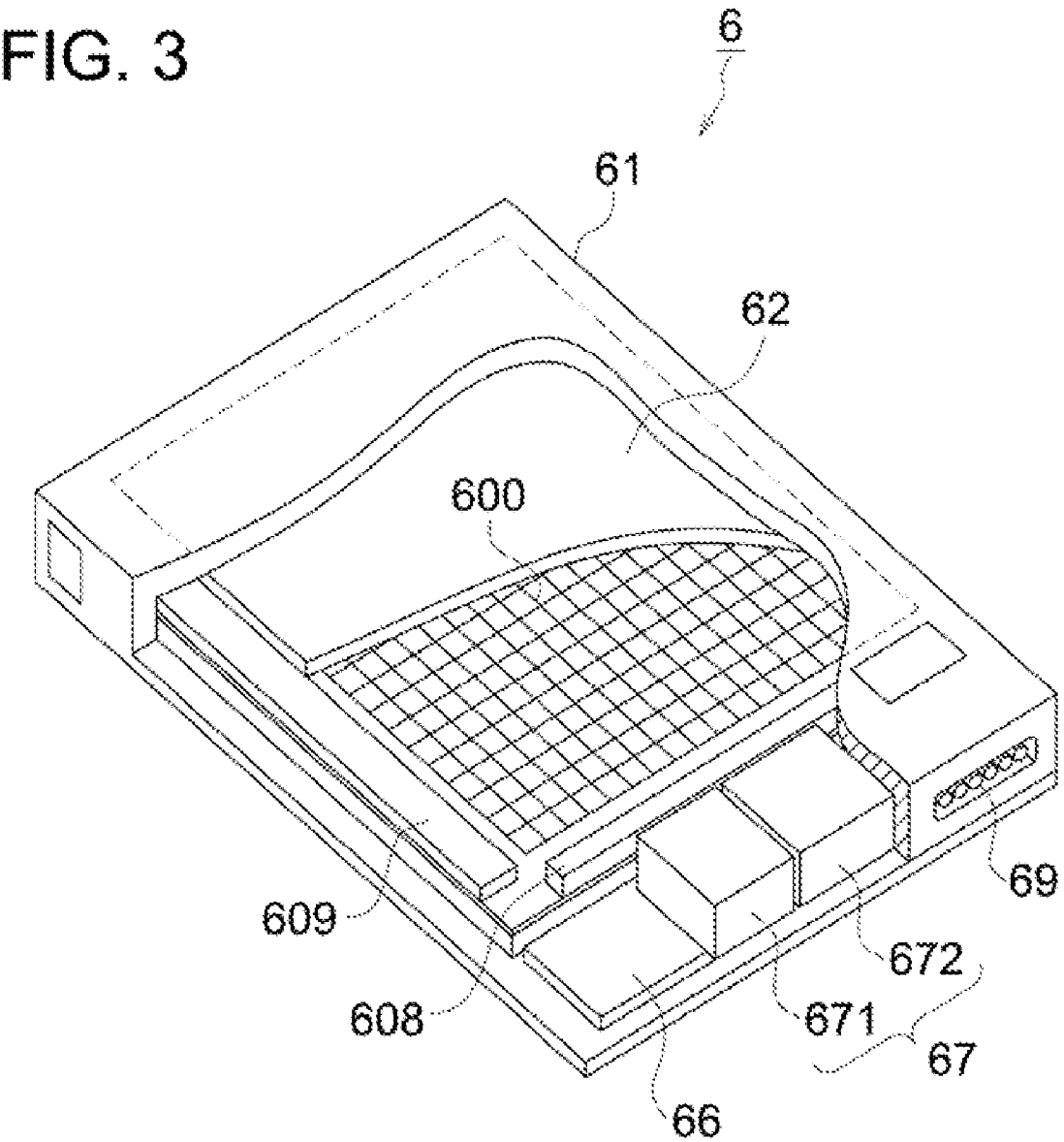
FIG. 3 is a perspective view of a radiation image detecting apparatus.
Figure 4:
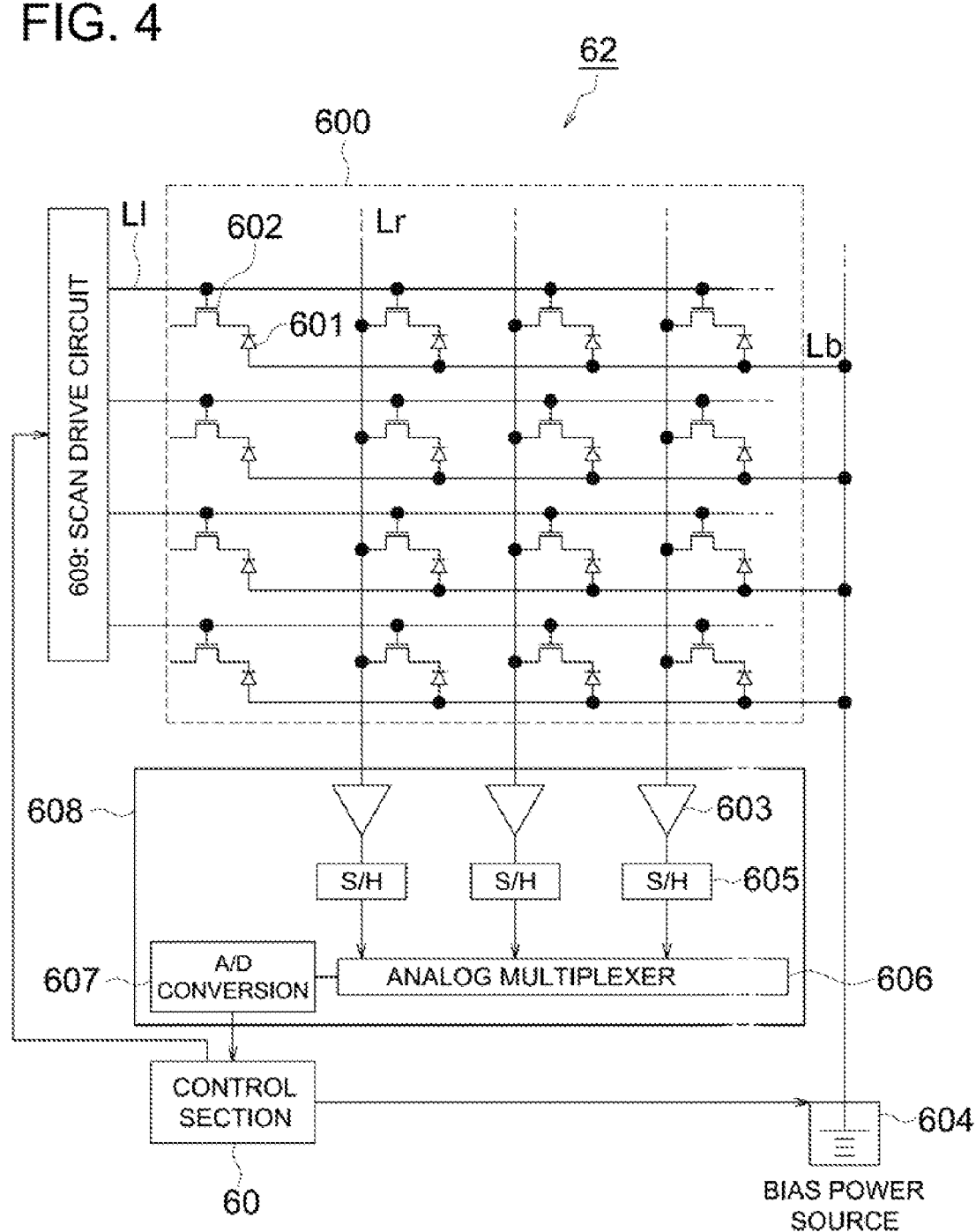
FIG. 4 is an equivalent circuit of the signal detecting section composed of two-dimensional array of a photoelectric conversion section.

Referring to FIG. 3 and FIG. 4, the following describes the structure of the radiation image detecting apparatus 6. FIG. 3 is a perspective view of a radiation image detecting apparatus 6. As shown in FIG. 3, the radiation image detecting apparatus 6 has a casing 61 for internal protection and is designed as a portable cassette structure.

The casing 61 contains a layer of imaging panel 62 as an image data generating section which converts the applied radiation into electric signal. The irradiated side of this imaging panel 62 is provided with a light emitting layer (not illustrated) that, emits light in response to the intensity of incoming radiation.

The light emitting layer is generally called the scintillator layer, and is mainly composed of a phosphor, for example. Based on the incoming radiation, it outputs the electromagnetic wave having a wavelength of 300 nm through 800 nm, namely, the electromagnetic wave (light) ranging from the ultraviolet rays to infrared rays including visible rays in the middle.

The side opposite to the side exposed to the radiation of this light emitting layer is provided with the signal detecting section 600 constructed of a matrix of photoelectric conversion sections that convert the electromagnetic wave (light) outputted from the light emitting layer, into the electric energy, store it, and output the image signal based on the stored electric energy. The signal outputted from one photoelectric conversion section corresponds to one pixel that is the minimum unit constituting the radiation image data.

The following describes the circuit configuration of the imaging panel 62. FIG. 4 is an equivalent circuit of the signal detecting section 600 consisting of two-dimensional array of a photoelectric conversion section. As shown in FIG. 4, the photoelectric conversion section is made of a photodiode 601 and a thin film transistor (TFT) 602 for extracting the electric signal by switching the electric energy stored in the photodiode 601. The extracted electric signal is amplified by an amplifier 603 until it can be read out by a signal reading circuit 608. The amplifier 603 is connected with a reset circuit (not illustrated) made of a TFT 602 and capacitor. The stored electric signal is reset by switching the TFT 602.

The scanning line L1 and signal line Lr are arranged between the photoelectric conversion sections constituting the pixel so as to be perpendicular to each other. One end of the aforementioned photodiode 601 is connected with a TFT 602, and is connected with a signal line Lr through the TFT 602. The other end of the photodiode 601 is connected with one end of the adjacent photodiode 601 which is arranged for each row, and is connected with the bias power source 604 through a common bias line Lb. One end of this bias power source 604 is connected with the control section 60. In response to the instruction from the control, section 60, a voltage is applied to the photodiode 601 through the bias line Lb.

The gate of the TFT 602 arranged on each row is connected with a common scanning line L1, and the scanning line L1 is connected with the control section so through the scan drive circuit 609 that transmits pulses to each photoelectric conversion element. Similarly, one end of the photodiode 601 arranged for each row is connected with the signal reading circuit 608 that is connected to the common signal line Lr and is controlled by the control section 60. Counting from the one closest to the imaging panel 62, the amplifier 603, sample hold circuit 605, analog multiplexer 606 and A/D converter 607 are arranged on the signal reading circuit 608 over the common signal line Lr.

At the time of signal reading, the scan drive circuit 609 is driven to turn on the TFT 602, whereby the electric charge stored in the photodiode 601 is transmitted to the amplifier 603 as an electric signal. This electric signal is amplified by the amplifier 603 until it can be defected by the signal reading circuit 608. The voltage of the amplifier 603 is stored temporarily in the sample hold circuit 605, and is then sent to the analog multiplexer 606.

The analog multiplexer 606 converts the obtained voltage to serial electric signal and sends it to the A/D converter 607, wherein this electric signal is converted into digital data. Thus, the radiation image data is generated by the imaging panel 62.

Going back to FIG. 3, the radiation image detecting apparatus 6 is further provided with an image storing section 66, power source 57, and charging terminal 69.

The image storing section 66 is made of a rewritable memory such as a nonvolatile memory and flash memory, and is capable of storing the radiation image data corresponding to several images through several tens of images outputted from the imaging panel 62. This image storing section 66 can be a built-in type memory or a removable memory such as a memory card.

The power source 67 supplies electric power to a plurality of drive sections (control section 60, imaging panel 62, image storing section 66, etc.) constituting the radiation image detecting apparatus 6. This power source 67 is formed of a standby battery 671 and rechargeable battery 672, for example. The battery 672 can be recharged by connecting a charging terminal 69 to a cradle (not illustrated).

FIG. 2(c) is a block diagram representing the major components of a radiation image detecting apparatus 6. As shown in FIG. 2(c), the control system of the radiation image detecting apparatus 6 includes a control section 60, imaging panel 62, image storing section 66, power source section 67, ROM 81, RAM 82, and communication section 83. These components are connected by the bus 84. Of these components, the imaging panel 62, image storing section 66 and power source section 67 have already been described, and will not be described below to avoid duplication.

The control section 60 is made up of a CPU, for example. It reads out the control program stored in the ROM 81 and loads it in the work area formed in the RAM 82. Thus, various components of the radiation image detecting apparatus 6 are controlled according to the control program.

The ROM 81 is constructed of a nonvolatile semiconducting memory, and stores the control program to be run by the control section 60 and various forms of programs.

In various forms of processing applied under the control of the control section 60, the RAM 82 forms a work area for temporarily storing the various forms of programs that can be read out from the ROM 81 and can be executed by the control section 60, inputted or outputted data, parameters and others.

The communication section 83 performs wireless communication of various forms of information with the console 7 and server 2 through the base station 5, using the wireless LAM conforming to the IEEE 802.11 Standard.

Embodiment 1

FIG. 9 is a flow chart representing the operation of the radiation image radiographing system 200 as a first embodiment. Referring to this diagram, the following describes how data of plural radiation images is generated by one radiation image detecting apparatus 6 and how the data of plural radiation images is transmitted to the console 7. In this embodiment, it is assumed that plural radiographing order information required for the radiographing operation has been inputted by a doctor or personnel in charge of reception and radiographing order information list of FIG. 5 is stored in the external storing apparatus of the RIS server 2.

Before starting the radiographing operation, an operator such as a doctor or radiographing technician operates the input operation section 18 of the console 7 to input the message indicating the start of radiographing. Upon receipt of the message indicating start of radiographing from the input operation section 18, the control section 14 of the console 7 receives the radiographing order information list stored in the external storing apparatus of the RIS server 2, and stores this radiographing order information list in the storing section 21 (Step S1). The input screen 171 for inputting the radiographing order information corresponding to the current radiographing operation is displayed on the display section 17 (Step S2).

FIG. 6 is an example showing that the input screen 171 for inputting the radiographing order information is indicated on a display section 17. As shown in FIG. 6, the input screen 171 is provided with a first radiographing order information display area 171a for displaying the radiographing order information list stored in the storing section 21. Each of the radiographing order information items given on the radiographing order information list contains the information of "radiographing order ID" P1, "patient ID" P2, "patient name" P3, "sex" P4, "age" P5, "ward" P6, "diagnosis department" P7, "radiographing region" P8, "radiographing direction" P9. While checking the first radiographing order information display area 171a of the display section 17, a technician operates the input operation section 18 and clicks on all the radiographing order information items scheduled as the current radiographing operation. Upon completion of inputting the radiographing order information, the technician clicks on the "Determine button" 171c.

Upon receipt of the input from the input operation section 18, the control section 14 of the console 7 selects the radiographing order information item having the "radiographing order ID" P1 of "001", out of the radiographing order information list stored in the storing section 21 (Step S3: selection device). A decision is made to see whether or not there is a predetermined relationship between this selected radiographing order information item and the other radiographing order information items stored in the storing section 21, in other words, whether or not the "patient ID" P2 included in the selected radiographing order information item is identical to the "patient ID" P2 contained in each of the other radiographing order information items (Step S4: determining device). To be more specific, in this Step, a decision is made to see whether or not "patient ID" P2 of the other radiographing order information items are "100085". Of the other radiographing order information items, the radiographing order information where the "patient ID" P2 is "100085" is indicated on the display section 17 as a determination result screen 172 (Step S5).

FIG. 7 is an example showing that the determination result screen 172 representing the result of determination step is displayed on a display section 17. As shown in FIG. 7, the upper portion of the determination result screen 172 is provided with the selected radiographing order information display area 172a showing the radiographing order information selected in Step S3. The center of the determination result screen 172 is equipped with the second radiographing order information display area 172b for displaying the radiographing order information items that have the "patient ID" P2 identical to the selected radiographing order information. Further, the lower portion of the determination result screen 172 is provided with a "Determine button" 172c and a "Return button" 172d. As will be described later, permission of additional selection is granted only to the radiographing order information item shown in the second radiographing order information display area 172b, and this corresponds to the permission device of the present invention.

While checking the second radiographing order information display area 172b of the display section 17, a technician operates the input operation section 18 to click on a desired radiographing order information item out of the radiographing order information items displayed on the second radiographing order information display area 172b. Normally, it is more effective to select plural radiographing order information items in one radiographing flow, and to perform plural radiographing in one operation. It will be assumed here that the technician has clicked on both the radiographing order information items having the "radiographing order ID" P1 of "002" and "003". When the radiographing order information has been inputted, the technician clicks on the "Determine button" 172c. When returning to the precious processing, the technician has to click on the "Return button" 172d.

Upon receipt of the input from the input operation section 18, the control section 14 of the console 7 additionally selects the radiographing order information items that have the "radiographing order ID" P1 of "002" and "003" (Step S6). It further establishes correlation between the radiographing order information selected in Step S3 and the radiographing order information selected in Step S6, and stores them in the storing section 21 (Step S7). Upon completion of storage in the storing section 21, a cassette ID input screen appears on the display section 17, indicating the message of "Input the cassette ID of the radiation, image detecting apparatus 6" (not illustrated).

Of the enabled apparatuses, the technician selects one radiation image detecting apparatus 6 meeting the current radiographing requirement. Then the technician operates the input operation section 18 and inputs the cassette ID of the radiation image detecting apparatus 6. Upon receipt of the input from the input operation section 18, the control section 14 of the console 7 establishes correlation between the inputted cassette ID and the three radiographing order information items stored in the storing section 21 in Step S7, and stores them in the storing section 21 (Step S8). The radiographing information contained in the radiographing order information is transmitted to the radiographing operation apparatus 4, and the console ID of the console 7 is sent to the radiation image detecting apparatus 6 through the base station 5 by wireless communication. Preparation for radiographing is now completed.

Upon completion of the aforementioned preparation for radiographing operation, the technician installs the selected radiation image detecting apparatus 6 on the detecting apparatus mounting port 11a of the radiographic stand 11 for lying position. In this case, the radiation image detecting apparatus 6 enters the radiographing standby state (Step S9). Further, the technician places the radiographing region of the patient 12 on the radiographic stand 11 for lying position to ensure that the radiographing region represented by the radiographing information will properly be positioned with respect to the radiation image radiographing apparatus 3. When the radiographing operation apparatus 4 is controlled based on the radiographing information received from the console 7, radiation conforming to the radiographing information is applied from the radiographing apparatus 3.

The control section 60 of the radiation image detecting apparatus 6 detects the radiation that has been emitted from the radiation image radiographing apparatus 3 and that has passed through the patient 12. The control section 60 generates the radiation image data in the aforementioned process, and this data is stored in the image storing section 66 (Step S10). This allows the image storing section 66 to store the radiation image data for one radiographing operation corresponding to one radiographing order information item. In the present embodiment, three radiographing order information items corresponding to the radiation image detecting apparatus 6 have been selected, as described above. Accordingly, the operation of Step S10 is repeated three times, and the radiation image data for three radiographing operations corresponding to three radiographing order information items are stored in the image storing section 66. It goes without saying that, when radiographing operation is repeated several times, radiographing operation can be performed, across a plurality of radiographing rooms.

Upon completion of radiographing operation (Step S11: Yes), the technician removes the radiation image detecting apparatus 6 from the detecting apparatus mounting port 11a of the radiographic stand 11 for lying position, and depresses the transmission button (not illustrated) of the radiation image detecting apparatus 6. Upon receipt of the input from the transmission button, the control section 60 of the radiation image detecting apparatus 6 adds the cassette ID to the radiation image data corresponding to three radiographing operations stored in the image storing section 66, and sends this information from the communication section 83 through the base station 5 by wireless communication (Step S12). In this case, the receiver of the radiation image data corresponding to three radiographing operations and cassette ID is determined according to the console ID received in advance. Here the console 7 is set as a receiver.

The control section 14 of the console 7 receives the radiation image data and cassette ID transmitted from the radiation image detecting apparatus 6 (Step S13). The radiation image data corresponding to three radiographing operations is subjected to the image processing such as analog-to-digital conversion, normalisation and gradation processing, and is stored in the storing section 21. Then the radiation image data corresponding to three radiographing operations stored in the storing section 21 and the radiographing order information correlated with the cassette ID in Step S8 are indicated on the display section 17 (Step S14).

While checking the display on the display section 21, the technician operates the input operation section 18 to establish correlation between the radiation image data corresponding to three radiographing operations and the three radiographing order information items. In the present embodiment, only the radiographing order information for one and the same patient is selected, as described above. Based on this radiographing order information, radiographing operation is performed. This arrangement allows the technician to identify each of the plural radiation image data items and to accurately identify the correlation between the radiation image data and radiographing order information item. To be more specific, normally, when one patient is radiographed several times, there is a very low possibility of overlapped radiographing of the same region or similar region in one radiographing flow. In the case of the radiation image data obtained from one and the same patient, therefore, even if data of radiation images has been stored simultaneously in one radiation image detecting apparatus 6, easy identification of the radiation image data can be ensured.

In response to the input from the input operation section 18, the control section 14 of the console 7 establishes correlation between the radiographing order information and radiation image data (Step S15). They are then stored in the storing section 21, and the present flow terminates.

As described above, in the present embodiment, a plurality of radiographing operations are performed using one radiation image detecting apparatus 6, whereby radiation image data corresponding to plural radiographing operations is generated. In the selection of the plural radiographing order information items corresponding to each of these radiation image data corresponding to plural radiographing operations, if one radiographing order information has been selected, a decision is made to see whether or not the "patient ID" P2 of the one radiographing order information and "patient ID" P2 of the other radiographing order information are identical to each other. Thus, additional selection of only the identical other radiographing order information is permitted. As described above, normally, when one patient is radiographed several times, there is a very low possibility of overlapped radiographing of the same region or similar region in one radiographing flow.

Thus, even if one and the same patient is radiographed several times by the one radiation image detecting apparatus 6, and the generated radiation image data corresponding to plural radiographing operations are stored simultaneously, when the radiation image data corresponding to plural radiographing operations is displayed on the console 7, the technician can identify the correlation between the radiation image data and radiographing order information item. Accordingly, even if there is a correlation error between the radiation image data and radiographing order information, the technician can easily find out the correlation error to establish correct correlation. This arrangement prevents confusion of radiation image data, and hence avoids a medical error.

When the radiographing order information is selected additionally, the aforementioned arrangement eliminates the need of the doctor making a decision on which radiographing order information item should be selected in order to identify the radiation image data. This enhances working efficiency.

The determination result screen 172 showing the result of decision is indicated on the display section 17, and the radiographing order information granted the permission of additional selection is inputted on this determination result screen 172. This arrangement reveals at a glance the radiographing order information item that can be additionally selected, and reduces the percentage of missing selection of the radiographing order information by the technician.

In the aforementioned embodiment, the information having the "patient ID" P2 identical to the "patient ID" P2 of the one selected radiographing order information item is set as the radiographing order information having a predetermined relationship with the one selected radiographing order information item, without the present invention being restricted thereto. For example, the radiographing order information item having the "radiographing region" P7 different from the "radiographing region" P7 contained in the one selected radiographing order information item, or the radiographing order information item having the "radiographing region" P7 and "radiographing direction" P8 wherein at least one of the "radiographing region" P7 and "radiographing direction" P8 is different from that of the one selected radiographing order information item can be set as the information having a predetermined relationship.

Even if data of plural radiation images obtained by radiographing different patients is stored in one radiation image detecting apparatus 6, this setting allows the technician to accurately identify the correlation between the radiation image data and radiographing order information. Hence, this arrangement allows radiographing operations to be performed in one radiographing flow across a plurality of patients, and contributes to further enhancement of radiographing efficiency, on the one hand. On the other hand, for example, if the L (left) and R (right) in the vertical direction (also called the CC) of the breast region are radiographed, identification of radiation image data cannot be achieved despite the different "radiographing direction" P8. When radiation image data cannot be identified, as in the case of the CC-L and CC-R of this breast region, simultaneous selection is prohibited. Thus, having a predetermined relationship in the present invention permits the setting to be changed as desired in response to particular work requirements, as long as the technician can identify the radiation image data.

In the aforementioned description, additional selection of radiographing order information is performed in response to the input from the input operation section 18 by the technician. As described above, in one radiographing flow, higher radiographing efficiency is ensured by selecting plural radiographing order information items and performing a plurality of radiographing operations in one step. Thus, it is also possible to make arrangements to perform automatic selection of all the radiographing order information having been granted the permission of additional selection. This arrangement eliminates the need of additional selection of the radiographing order information by the doctor and improves work efficiency. At the same time, this arrangement ensures automatic selection of all the radiographing order information which can be radiographed in one radiographing flow, and avoids missing selection of radiographing order information.

Embodiment 2

In the first embodiment, the console 7 is used to determine whether or not there is predetermined correlation between the one radiographing order information item and the other radiographing order information item. In the present embodiment, the radiation image detecting apparatus 6 is used to serve this function. The basic apparatus structure of the present embodiment is the same as that of the first embodiment. To avoid duplication, the following describes only the differences from the first embodiment.

As shown in FIG. 2(c), the control system of the radiation image detecting apparatus 6 has a control section 60, imaging panel 62, image storing section 66, power source section 67, ROM 81, RAM 82, communication section 83 and others. These components are linked by the bus 84. Of these, the imaging panel 62, image storing section 66, power source section 67, ROM 81, and communication section 83 have the same functions as those in the first embodiment, and will not be described here.

The RAM 82 forms a work area for temporarily storing various forms of programs that are executed under the control of the control section 60, input or output data, parameters and others. As will be described later, it also temporarily stores the radiographing order information sent from the console 7. In the present embodiment, the RAM 82 corresponds to the radiographing order information storing section.

The control section 60 reads out the control program stored in the ROM 81, and loads it in the work area formed inside the RAM 82. The control section 60 controls various components of the radiation image detecting apparatus 6 according to the control program, and determines whether or not there is a predetermined relationship between the one radiographing order information item stored in the ram 82, and the other radiographing order information subsequently transmitted from the console 7. The control section 60 then grants permission of additional selection only to the other radiographing order information item having a predetermined relationship. In other words, in the present embodiment, this control section 60 corresponds to the determining device and permission device.

Figure 10:
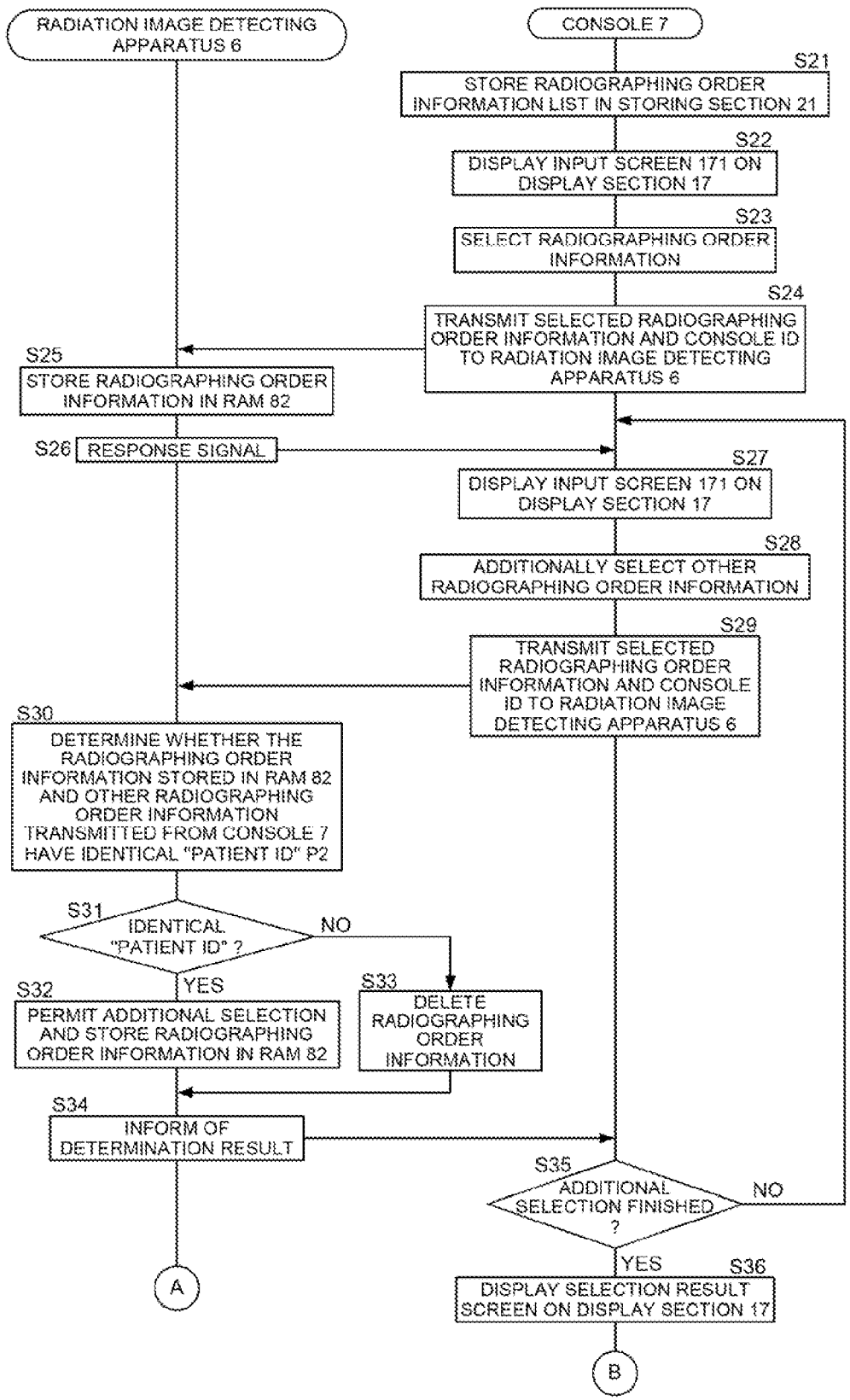
FIG. 10 is a flow chart representing the operation of the radiation image radiographing system as a second embodiment.
Figure 11:
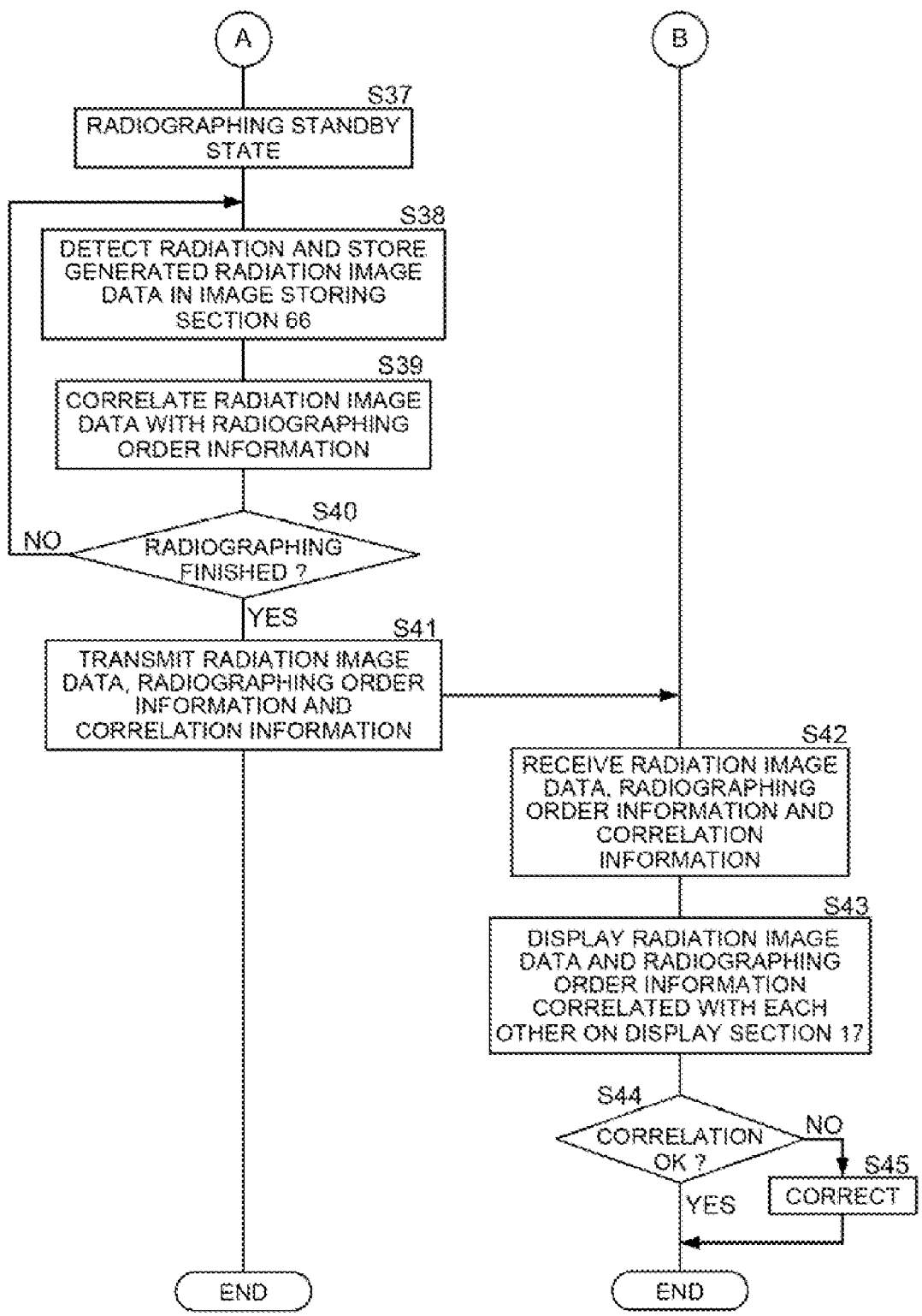
FIG. 11 is a flow chart representing the operation of the radiation image radiographing system as a second embodiment.

FIG. 10 and FIG. 11 are flow charts representing the operation of the radiation image radiographing system 200 as a second embodiment. Referring to these charts, the following describes a series of operations wherein plural radiation image data is generated by the radiation image detecting apparatus 6 and is transmitted to the console 7.

Before starting the radiographing operation, a technician operates the input operation section 18 of the console 7 to input the information of starting the radiographing operation. Upon receipt of the message of starting the radiographing operation from the input operation section 18, the control section 14 of the console 7 receives the radiographing order information list stored in the external storing apparatus of the RIS server 2, and stores this radiographing order information list into the storing section 21 (Step S21). As shown in FIG. 6, the input screen 171 for inputting the radiographing order information corresponding to the relevant radiographing operation is displayed on the display section 17 (Step S22). In this case, similarly to the case of the first embodiment, it is assumed that the radiographing order information item having the "radiographing order ID" P1 of "001" is clicked.

Upon receipt of the input from the input operation section 18, the control section 14 of the console 7 selects the radiographing order information item having a "radiographing order ID" P1 of "001" from the radiographing order information list stored in the storing section 21 (Step S23: selection device). The one selected radiographing order information item and the console ID of the console 7 are transmitted to the radiation image detecting apparatus 6 through the base station 5 by wireless communication (Step S24).

Having received the one radiographing order information item and console ID from the console 7, the control section 60 of the radiation image detecting apparatus 6 stores the one radiographing order information item as the selected radiographing order information in the RAM 82 (Step S25). The console 7 containing the console ID having been received is set as a receiver and the response signal denoting the receipt is transmitted to the console 7 (Step S26).

Upon receipt of the response signal from the radiation image detecting apparatus 6, the control section 14 of the console 7 again displays the input screen 171 on the display section 17 (Step S27). In this Step, it is preferred to make arrangements that the radiographing order information selected in Step S23 is not displayed, or cannot be inputted.

While checking the input screen 171, the technician operates the input operation section 18 to click on the other radiographing order information item different from the radiographing order information selected in Step S23. Here, it is assumed that the technician has clicked on the radiographing order information item having a "radiographing order ID" P1 of "002".

Upon receipt of input from the input operation section 18, the control section 14 of the console 7 additionally selects the radiographing order information having a "radiographing order ID" P1 of "002" from among the plural radiographing order information items stored in the storing section 21 (Step S28), and transmits the radiographing order information selected in Step S28 and the console ID of the console 7 to the radiation image detecting apparatus 6 (Step S29).

Having received the radiographing order information and console ID from the console 7, the control section 60 of the radiation image detecting apparatus 6 determines whether or not the "patient IDs" P2 contained in this radiographing order information item and the radiographing order information stored in the RAM 82 in the Step S25 are identical with each other (Step S30: determining device). Since the "patient IDs" P2 are identical to each other as "100085" (Step S31: Yes), permission of additional selection is granted to the received radiographing order information and the radiographing order information is stored in the RAM 82 (Step S32: permission device). Then the response signal denoting the result of determination is transmitted to the console 7 (Step S34). In Step S28, if the radiographing order information having the "radiographing order ID" P1 of "004" has been selected, the "patient ID" P2 of this radiographing order information item is "100125" and is not identical (Step S31: No). Accordingly, permission of additional selection is not granted to the radiographing order information, which is then deleted (Step S33). Then the response signal denoting this result of determination is transmitted to the console 7 (Step S34).

Upon receipt of the response signal from the radiation image detecting apparatus 6, the control section 14 of the console 7 prompts the technician to determine whether or not permission of additional selection is further granted to the other radiographing order information (Step S35). When the other radiographing order information is to be selected (Step S35: No), the aforementioned Step S27 through Step S34 are repeated. Upon completion of the additional selection of radiographing order information by repeating the aforementioned selection procedure (Step S35: Yes), the display section 17 displays the selection result screen (not illustrated) denoting the radiographing order information to which the permission of selection has been granted (Step S36). Then preparation for radiographing terminates. The radiographing information contained in the radiographing order information is sent to the radiographing operation apparatus 4.

As described above, plural radiographing order information items are normally selected in one radiographing flow, and a plurality of radiographing operations are performed in one step. This ensures higher radiographing operation efficiency. Accordingly, in the present embodiment, similarly to the case of the first embodiment, it is assumed that all the radiographing order information items having been granted the permission of additional selection, namely, three radiographing order information items having "radiographing orders ID" P1 of "001", "002" and "003" are selected by the radiation image detecting apparatus 6.

Upon completion of the preparation for the aforementioned radiographing operation, the technician mounts the selected radiation image detecting apparatus 6 on the detecting apparatus mounting port 11a of the radiographic stand 11 for lying position. In this case, the radiation image detecting apparatus 6 enters the radiographing standby state (Step S37). According to the order of selection of the radiographing order information selected by the radiation image detecting apparatus 6, the radiographing operation apparatus 4 is controlled based on the radiographing information received from the console 7, whereby radiation in response to the control information is issued from the radiation image radiographing apparatus 3.

The control section 60 of the radiation image detecting apparatus 6 detects the radiation that, has been issued from the radiation image radiographing apparatus 3 and has passed through the patient 12. The control section 60 then generates radiation image data and stores it in the image storing section 66 (Step S38). Correlation is established between the radiation image data and radiographing order information according to the sequential order wherein the radiation image data is generated, and the sequential order wherein the radiographing order information item is selected (Step S39). This correlation information is stored in the RAM 82. In the present embodiment, as described above, the three radiographing order information items have been selected, and therefore, the operations of Step S37 and Step S38 are repeated three times. Upon completion of radiographing (Step S40: Yes), radiation image data, radiographing order information and correlation information are sent to the console 7 (Step S41).

The control section 14 of the console 7 receives the radiation image data, radiographing order information and correlation information from the radiation image detecting apparatus 6 (Step S42), and stores them into the storing section 21. Based on the correlation information, the control section 14 displays a confirmation screen (not illustrated) denoting the correlation between the radiation image data and radiographing order information on the display section 17 (Step S43).

The technician checks the confirmation screen appearing on the display section 17. If there is no correlation error (Step S44: Yes), the flow terminates. If there is a correlation error (Step S44: No), the technician corrects the error using the input operation section 18 (Step 345). In the present embodiment, only the radiographing order information of one and the same patient is selected by the radiation image detecting apparatus 6. The radiographing operation is performed according to this radiographing order information. This allows the technician to identify data of each of the plural radiation images. When there is a correlation error between the radiation image data and radiographing order information, the technician can easily find it out.

As described above, in the present embodiment, the radiographing order information is sent to the radiation image detecting apparatus 6. Radiographing operation is performed in the sequential order in which the radiographing order information has been selected (sent), whereby precise correlation is established between the radiographing order information and radiation image data. However, when performing multiple radiographing operations making the maximum use of the characteristics of the radiation image detecting apparatus 6, it is difficult for the technician to correctly remember the order of a great number of radiographing order information items having been selected. This increases the possibility of the technician confusing the correlation between the sequential order of radiographing order information items and the sequential order of radiographing operations. By contrast, when a display section for displaying radiographing order information is provided on the radiation image detecting apparatus 6, and radiographing operation is performed by checking the aforementioned radiographing order information appearing on this display section, there is no need for the technician to remember the aforementioned sequential order of radiographing order information items. However, this arrangement requires a display section to be provided on the radiation image detecting apparatus 6, and hence increases the cost of the apparatus. Further, the apparatus tends to break down earlier.

To solve this problem, in the present embodiment, when selecting the plural radiographing order information items corresponding to each of radiation image data items for plural radiographing operations, the radiation image detecting apparatus 6 determines whether or not the "patient ID" P2 of one radiographing order information item is identical to the "patient ID" P2 of the other radiographing order information item. Permission of additional selection is granted only to the identical other radiographing order information item. Normally, in case of one patient, there is a few possibility of radiographing the same or similar regions.

Thus, even if one patient is radiographed several times by one radiation image detecting apparatus 6 and the generated radiation image data corresponding to plural radiographing operations is stored simultaneously, when this radiation image data corresponding to plural radiographing operations is displayed on the console 7, the technician is allowed to identify the correct correlation between the radiation image data and radiographing order information. Accordingly, even if the radiation image detecting apparatus 6 has confused the correlation between the radiation image data and radiographing order information, the technician easily takes notice of the incorrect correspondence and is allowed to correct the error. This prevents confusion of radiation image data, and eliminates the need of having to install a display section on the radiation image detecting apparatus 6, with the result that a less costly indestructible apparatus is provided.

Further, when additionally selecting the radiographing order information, there is no need for the doctor to determine which radiographing order information should be selected in order to identify radiation image data. This arrangement enhances the work efficiency.

In the present embodiment, when additionally selecting the radiographing order information, the other radiographing order information items are sent one by one to the radiation image detecting apparatus 6 by the console 7, and the other radiographing order information items having been sent are identified one by one by the radiation image detecting apparatus 6. However, for example, it is also possible to make such arrangements that, subsequent to transmission of one radiographing order information item, the other radiographing order information items are transmitted collectively from the console 7, and are collectively identified by the radiation image detecting apparatus 6, Further, the radiographing order information item having the "patient ID" P2 identical to the "patient ID" P2 of the one selected radiographing order information item has been set as the radiographing order information having a predetermined relationship with the one radiographing order information item having been selected. However, it goes without saying that the present invention is not restricted thereto, similarly to the case of the first embodiment.

Embodiment 3

Figure 12:
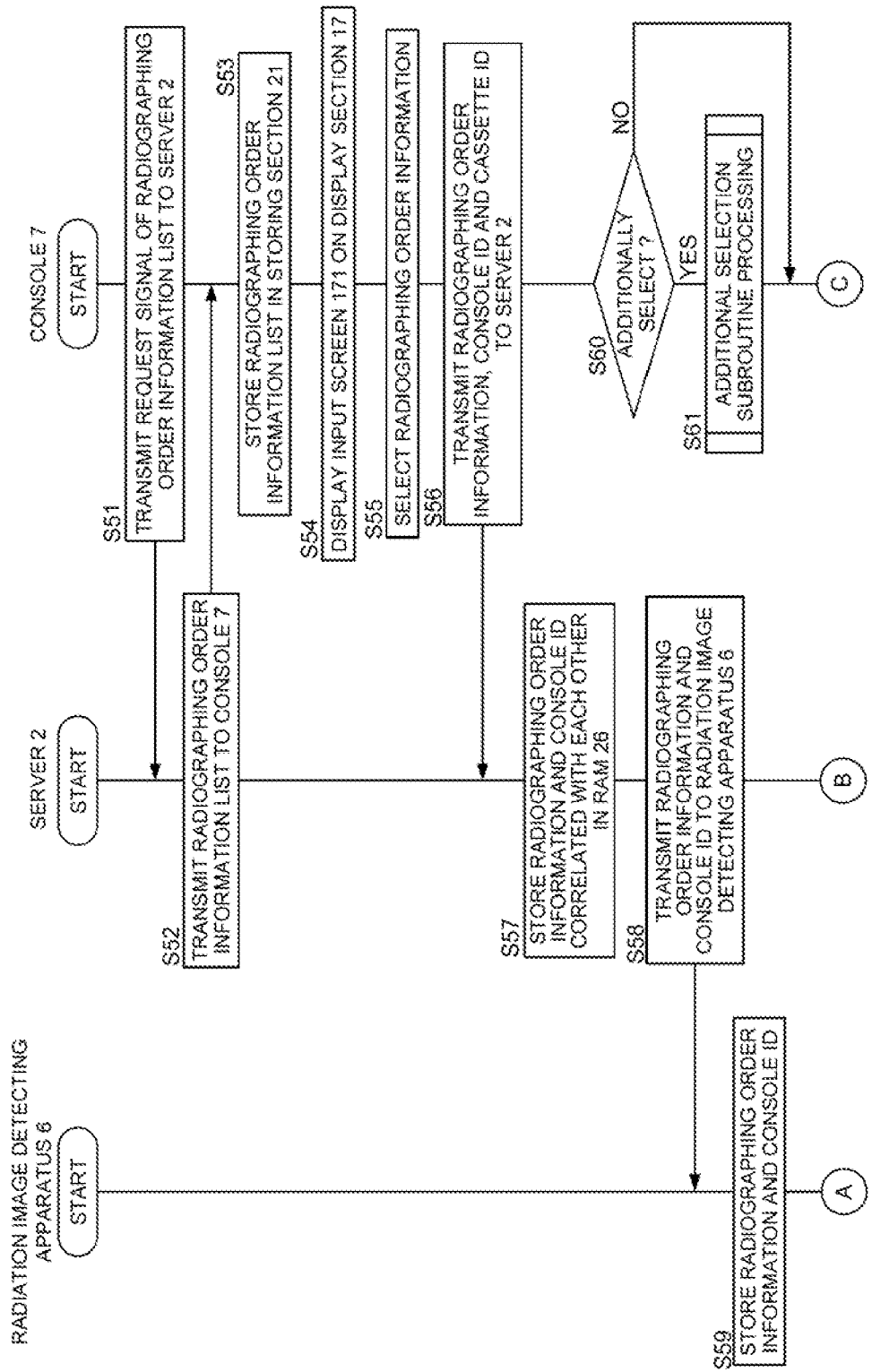
FIG. 12 is a flow chart representing the operation of the radiation image radiographing system as a third embodiment.
Figure 13:
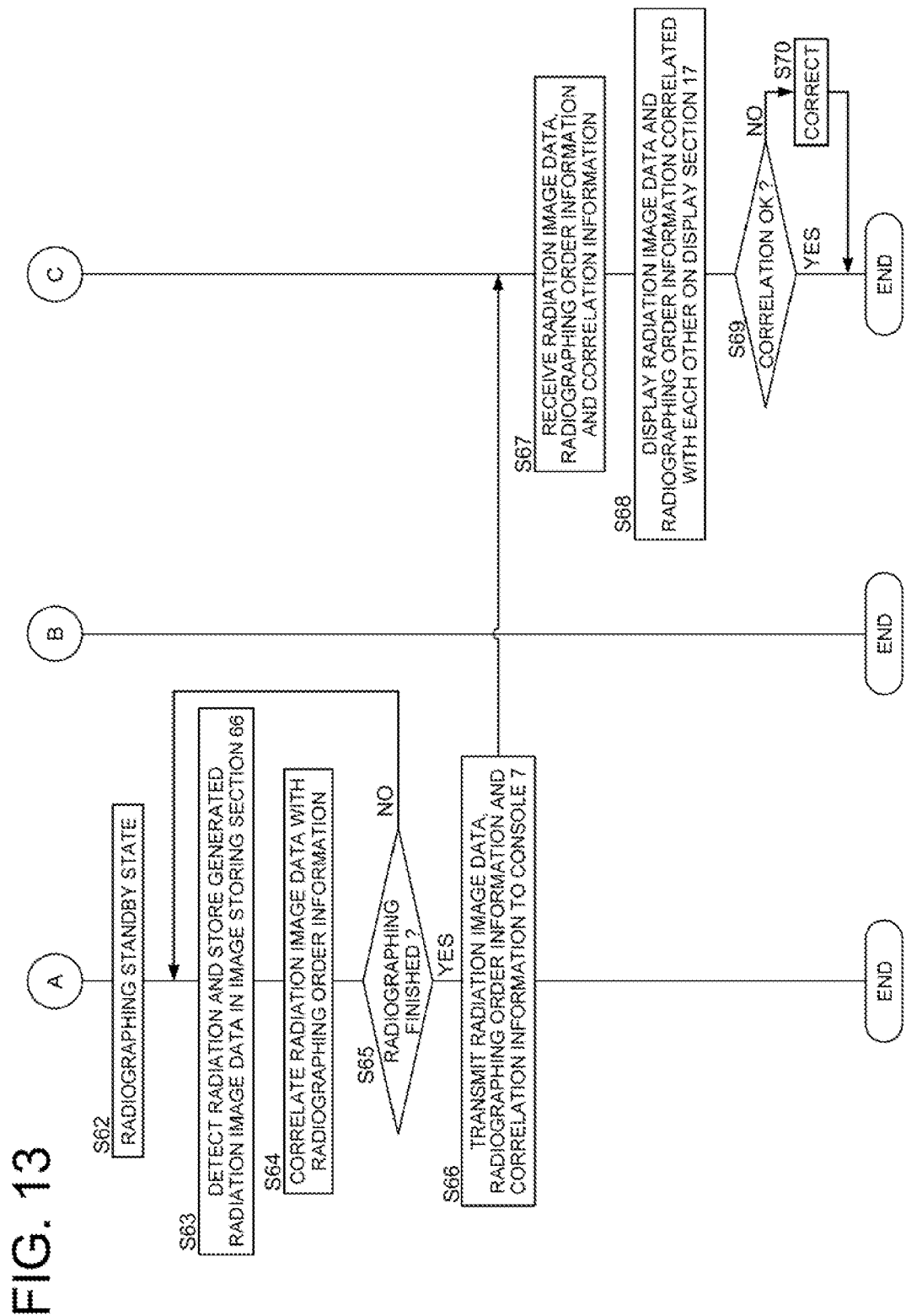
FIG. 13 is a flow chart representing the operation of the radiation image radiographing system as a third embodiment.
Figure 14:
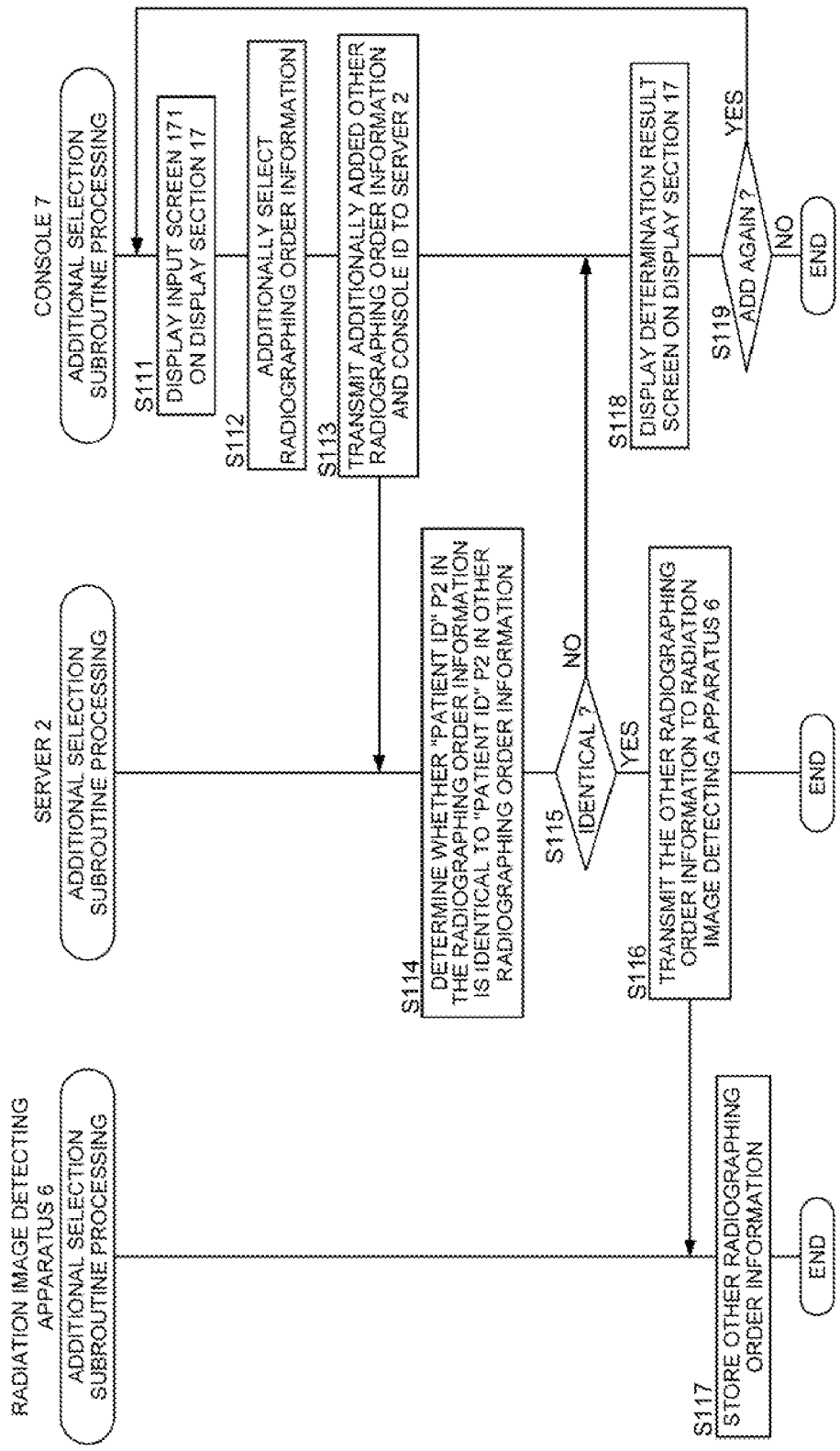
FIG. 14 is a flow chart representing the additional selection subroutine.

FIGS. 12 through 14 are flow charts representing the operation of the RIS 1. Referring to these drawings, the following describes a series of operations wherein data of plural radiation images is generated by one radiation image detecting apparatus 6, and the data of plural radiation images is sent to the console 7. In the present embodiment, the doctor or other personnel in charge of reception operates the input operation section 29 of the server 2 in advance, whereby plural radiographing order information items related to radiographing is inputted and the radiographing order information list of FIG. 5 is stored in the radiographing order information storing section 28 of the server 2. For simplicity, one console 7 will be taken up in the following description. A plurality of consoles connected to the server 2 are also capable of similar processing.

As shown in FIG. 7, before starting the radiographing, the operator such as a doctor or a radiographing technician operates the input operation section 18 of the console 7, and inputs the information notifying that the radiographing will start. Upon receipt of the information from the input operation section 18 notifying that the radiographing will start, the control section 14 of the console 7 transmits a request signal for the radiographing order information list to the server 2 (Step S51).

Upon receipt of the request signal from the console 7, the control section 25 of the server 2 transmits to the console 7, the radiographing order information list stored in the radiographing order information storing section 28 (Step S52). Upon receipt of the radiographing order information list from the server 2, the control section 14 of the console 7 stores this radiographing order information list in the storing section 21 (Step S53), and allows the display section 17 to display the input screen 171 for inputting the radiographing order information corresponding to the radiographing of this time (Step S54).

FIG. 6 is an example showing that the input screen 171 for inputting the one radiographing order information item is indicated on a display section 17.

While checking the first radiographing order information display area 171*a* of the display section 17, a technician operates the input operation section 18 and clicks on the item displayed for the radiographing order information corresponding to the relevant current radiographing. It is assumed here that the radiographing order information item having a "radiographing order ID" P1 of "001" has been clicked. If there is no error in the selection of this radiographing order information, the technician clicks on the determine button 171*b*. If the selection of the radiographing order information contains any error, the technician clicks on the cancel button 171c and makes a correct selection.

In response to the input from the input operation section 18, the control section 14 of the console 7 selects the radiographing order information having a "radiographing order ID" P1 of "001" from the radiographing order information list stored in the storing section 21 (Step S55: selection device). The one selected radiographing order information item, the console ID as the identification information of the console 7, and the cassette ID as the identification information of the radiation image detecting apparatus 6 to be used are transmitted to the server 2 (Step S56).

Upon receipt of information from the console 7, the control section 25 of the server 2 establishes correlation between the one radiographing order information item and the console ID and stores them into the RAM 26 (Step S57). Based on the cassette ID, the radiation image detecting apparatus 6 is set as a receiver, and the one radiographing order information item and console ID stored in the SAM 26 are transmitted thereto (Step S58).

Upon receipt of the radiographing order information and console ID from the server 2, the control section of the radiation image detecting apparatus 6 stores them in the storing section (Step S59).

Upon completion of selecting the one radiographing order information item, the control section 14 of the console 7 displays on the display section 17, the screen for prompting the technician to determine whether or not radiographing order information should be additionally selected (not illustrated). If an input has been given from the input operation section 18 notifying the intention of additional selection (Step S60: Yes), additional selection subroutine processing is executed (Step S61).

The following describes the additional selection subroutine processing. FIG. 14 is a flow chart representing the additional selection subroutine processing.

As shown in FIG. 14, upon completion of the input of additional selection from the input operation section 18, the control section 14 of the console 7 displays the input screen 171 on the display section 17 (Step S111). It is preferred that, in this Step, the radiographing order information selected in Step S55 is not displayed or cannot be inputted.

While checking the input screen 171, the technician operates the input operation section 18, and clicks on the other radiographing order information item which is different from the radiographing order information selected in Step S55. It is assumed here that the radiographing order information item having a "radiographing order ID" P1 of "002" has been clicked.

Upon receipt of the input from the input operation section 18, the control section 14 of the console 7 additionally selects the radiographing order information having a "radiographing order ID" P1 of "002" from the plural radiographing order information items stored in the storing section 21 (Step S112). The other radiographing order information additionally selected and the console ID of the console 7 are transmitted to the server 2 (Step S113).

Upon receipt of the other radiographing order information and console ID from the console 7, the control section 25 of the server 2 calls up the one radiographing order information item stored in the RAM 26 in Step S57, based on this console ID, and determines whether or not the one radiographing order information item and the other radiographing order information have a predetermined relationship (Step S114: Determining device). To put it more specifically, the control section 25 of the server 2 determines whether or not the "patient ID" P2 contained in the one radiographing order information item is identical to the "patient ID" P2 contained in the other radiographing order information item, in other words, whether or not the "patient ID" P2 of the other radiographing order information is "100085". The one radiographing order information item and the other radiographing order information item have a "patient ID" P2 of "100085", and are identical to each other (Step S115: Yes). Thus, permission of additional selection of the other radiographing order information is assumed to have been granted, and the other radiographing order information is sent to the radiation image detecting apparatus 6 (Step S116: permission device). If the "patient ID" P2 of the one radiographing order information item and that of the other radiographing order information item are not identical to each other (Step S115: No), permission of additional selection of the other radiographing order information is not granted, and hence, other radiographing order information is not sent to the radiation image detecting apparatus 6.

Upon receipt of the other radiographing order information from server 2, the control section of the radiation image detecting apparatus 6 establishes its correlation with the one radiographing order information item, and stores them in the storing section (Step S117). The control section 14 of the console 7 receives the determination result signal from the server 2, and displays the determination result screen (not illustrated) indicating the result of determination on the display section 17 (Step S118). If there is an additional selection of the radiographing order information again (Step S119: Yes), the procedures of the aforementioned Steps S111 through S118 are repeated. Normally, in one radiographing operation flow, higher radiographing efficiency can be achieved by selecting plural radiographing order information items and performing a plurality of radiographing operations in one step. Here it is assumed that the radiographing order information items having "radiographing orders ID" P1 of "002" and "003" are additionally selected and are stored in the storing section of the radiation image detecting apparatus 6. Each of the aforementioned other radiographing order information items has a "patient ID" P2 which is different from that of the one radiographing order information item, and therefore, permission of additional selection is not granted in the present embodiment.

As described above, upon completion of selection of the radiographing order information, the control section 25 of the server 2 transmits to the radiographing operation apparatus 4, the radiographing information contained in the selected radiographing order information, and the preparation for radiographing is now completed. Upon completion of the preparation for the radiographing, the technician mounts the selected radiation image detecting apparatus 6 on the detecting apparatus mounting port 11a of the radiographic stand 11 for lying position. In this case, the radiation image detecting apparatus 6 enters the radiographing standby state (Step S62). The technician places the radiographing region of the patient 12 on the radiographic stand 11 for lying position so that the radiographing region indicated by the radiographing information will be properly located with respect to the radiation image radiographing apparatus 3. Based on the radiographing information received from the console 7, the radiographing operation apparatus 4 is controlled according to the sequential order of selection of the selected radiographing order information items, whereby radiation is applied based on the control information from the radiation image radiographing apparatus 3.

The control section 60 of the radiation image detecting apparatus 6 detects the radiation having been applied from the radiation image radiographing apparatus 3 and having passed through the patient 12. In the aforementioned process, radiation image data is generated and is stored in the image storing section 66 (Step S63). This means that the image storing section 66 has stored the radiation image data for one radiographing operation corresponding to the one radiographing order information item. Based on the sequential order of the radiation image data being generated and the sequential order of the radiographing order information being selected, correlation is established between the radiation image data and radiographing order information (Step S64), and this correlation information is stored in the storing section. In the present embodiment, as described above, three radiographing order information items have been selected corresponding to the radiation image detecting apparatus 6, and therefore, the operations of Steps S63 and S64 are repeated three times, and the radiation image data for the three radiographing operations corresponding to the three radiographing order information items is stored in the image storing section 66. At the time of plural radiographing, it goes without saying that radiographing operation can be performed across a plurality of radiographing rooms.

Upon completion of radiographing (Step S65: Yes), the technician removes the radiation image detecting apparatus 6 from the detecting apparatus mounting port 11a of the radiographic stand 11 for lying position, and depresses the transmission button (not illustrated) of the radiation image detecting apparatus 6. Upon receipt of the input from the transmission button, the control section 60 of the radiation image detecting apparatus 6 attaches the cassette ID to the radiation image data for three radiographing operations stored in the image storing section 66, and sends from the communication section 83 through the base station 5 by wireless communication (Step S66). In this case, the receiver of the radiation image data for three radiographing operations and the cassette ID is determined by the console ID having been received in advance. Here, the console 7 is set as a receiver.

The control section 14 of the console 7 receives the radiation image data, radiographing order information and correlation information from the radiation image detecting apparatus 6 (Step S67), and stores them in the storing section 21. Based on the correlation information, the confirmation screen (not illustrated) showing the correlation between the radiation image data and radiographing order information is indicated on the display section 17 (Step S68).

The technician checks the confirmation screen, appearing on the display section 17. If there is no error in the correlation (Step S69: Yes), this flow terminates. If there is any error (Step S69: No), the technician operates the input operation section 18 to correct the error (Step S70). In the present embodiment, as described above, the radiographing order information for one patient is selected. Based on this radiographing order information, radiographing operation is performed. This arrangement allows the technician to identify each of the plural radiation image data items. Thus, even if there is an error in the correlation between the radiation image data and radiographing order information in the radiation image detecting apparatus 6, the technician is allowed to identify the correlation between radiation image data and radiographing order information, and to ensure correct correlation.

As described above, in the present embodiment, the radiographing order information is sent to the radiation image detecting apparatus 6. If radiographing operation is performed in the sequential order in which the radiographing order information has been selected (sent), precise correlation is established between the radiographing order information and radiation image data. However, when performing multiple radiographing operations making the maximum use of the characteristics of the radiation image detecting apparatus 6, it is difficult for the technician to correctly remember the sequential order of a great number of radiographing order information items having been selected. This increases the possibility of the technician confusing the correlation between the sequential order of radiographing order information items and the sequential order of radiographing operations. By contrast, when a display section for displaying radiographing order information is provided on the radiation image detecting apparatus 6, and radiographing operation is performed by checking the aforementioned radiographing order information appearing on this display section, there is no need for the technician to remember the aforementioned order of radiographing order information items. However, this arrangement requires a display section to be provided on the radiation image detecting apparatus 6, and hence increases the cost of the apparatus. Further, the apparatus tends to break down earlier.

In the present embodiment, when selecting plural radiographing order information item corresponding to radiation image data for plural radiographing operations, in the radiation image detecting apparatus 6, a decision is made to see whether or not the "patient ID" P2 of the one radiographing order information item and that of the other radiographing order information item are identical to each other. Permission of additional selection is granted only to the other radiographing order information item having the identical "patient ID" P2.

Normally, when one patient is radiographed several times, there is a fewer possibility of overlapped radiographing of identical or similar regions in one radiographing flow. Even if one patient is radiographed several times by one radiation image detecting apparatus 6 and the generated radiation image data corresponding to plural radiographing operations are stored simultaneously, radiation image data can be easily identified by the technician. Thus, even if there is an error in correlation between the radiation image data and radiographing order information in the radiation image detecting apparatus 6, the technician easily takes note of the correlation error, and corrects the error. In this sense, this arrangement prevents confusion of the radiation image data. Further, there is no need of installing a display section on the radiation image detecting apparatus 6, with the result that a less costly indestructible apparatus is provided.

Further, the server 1 determines whether or not the "patient ID" P2 of the one radiographing order information item and the "patient ID" P2 of the other radiographing order information item identical to each other. This arrangement eliminates the need of installing a device for determination on each of a plurality of consoles 7 and radiation image detecting apparatuses 6. Thus, this arrangement simplifies the system structure and facilitates introduction into the existing system, with the result that a less costly system can be provided.

When the radiographing order information is additionally selected, there is no need for the doctor to determine which radiographing order information should be selected in order to identify the radiation image data. This enhances work efficiency.

In the aforementioned embodiment, when selecting the one radiographing order information in Step S55, the technician operates the input operation section 18 of the console 7 and inputs the one radiographing order information item. The control section 14 selects the one radiographing order information item inputted from the input operation section 18 as one radiographing order information item, and transmits it to the server 2. Further, when additionally selecting the radiographing order information item, after the aforementioned one radiographing order information item has been transmitted to the server 2, the control section 14 receives the input of radiographing order information to be additionally selected from the input operation section 18 separately in Step S61, and transmits this radiographing order information to the server 2. However, the present invention is not restricted to this arrangement. It is also possible to make such arrangements that the one radiographing order information item and additionally selected radiographing order information are inputted simultaneously by the input operation section 18, and they are transmitted together to the server 2.

To put it more specifically, at the time of inputting one radiographing order information item, if the technician operates the input operation section 18 and inputs plural radiographing order information items together, the control section 14 of the console 7 selects the radiographing order information having received first, as the one radiographing order information item. After that, the control section 14 of the console 7 transmits to the server 2, all the radiographing order information having been inputted by the input operation section 18, and the control section 25 of the server 2 determines whether or not the one radiographing order information item selected by the console 7 has a predetermined relationship with the radiographing order information items of all radiographing order information having been received, other than the aforementioned one radiographing order information. Such an arrangement abovementioned is also possible. Further, it is also possible to make such arrangements that, when plural radiographing order information items have been inputted from the input operation section 18, the one radiographing order information item is not selected. For example, when plural radiographing order information is transmitted together to the server 2, the first transmitted radiographing order information may be selected as the one radiographing order information item. Then the control section 25 of the server 2 transmits the one radiographing order information item and the radiographing order information determined as having a predetermined relationship, to the radiation image detecting apparatus 6, and notifies the console 7 of the radiographing order information determined as having no predetermined relationship. Then the determination result screen is displayed on the display section 17 of the console 7.

In the aforementioned description, the radiographing order information item having the "patient ID" P2 identical to the "patient ID" P2 of the one selected radiographing order information item is set as the radiographing order information item having a predetermined relationship with the one selected radiographing order information item. It goes without saying that the present invention is not restricted thereto. For example, the radiographing order information item having the "radiographing region" P7 different from the "radiographing region" P7 contained in the one selected radiographing order information item, or the radiographing order information item having the "radiographing region" P7 and "radiographing direction" P8 wherein at least one of the "radiographing region" P7 and "radiographing direction" P8 is different from ones of the one selected radiographing order information item can be set as the radiographing order information item having a predetermined relationship with the one selected radiographing order information item.

Even if data of plural radiation images obtained by radiographing different patients have been stored simultaneously in one radiation image detecting apparatus 6, the aforementioned setting allows the technician to identify the correlation between the radiation image data and radiographing order information. This permits the doctor to perform radiographing operations across a plurality of patients in one radiographing flow, with the result that radiographing efficiency is further enhanced. In the meantime, for example, when radiographing the L (left) and R (right) in the vertical direction (also called "CC") of the breast region, the radiation image data cannot be identified, even if there is a difference in the "radiographing direction" P8. When radiation image data cannot be identified as in the case of the CC-L and CC-R of this breast region, simultaneous selection is prohibited. As described above, having a predetermined relationship in the present invention permits the possibility of adequate setting in response to the individual work form, to the extent that the technician can identify the radiation image data.

At the time of additional selection of the radiographing order information, each of the radiographing order information items having been inputted through the input operation section 18 of the console 7 is identified one by one, as explained with respect to the additional selection subroutine in Step 61. However, as described above, in one radiographing flow, radiographing efficiency is enhanced when plural radiographing order information items are selected, and a plurality of radiographing operations are performed together. Thus, it is also possible to make such arrangements that, upon receipt of the one radiographing order information, the server 2 automatically identifies the one radiographing order information item and plural radiographing order information items stored in the server 2 collectively. This arrangement eliminates the need of radiographing order information being additionally selected by the doctor. Thus, the work efficiency is enhanced, and all the radiographing order information items to be used for radiographing possible in one radiographing flow are automatically selected, with the result that there is no possibility of omission in the selection of radiographing order information.

Embodiment 4

Figure 1B:
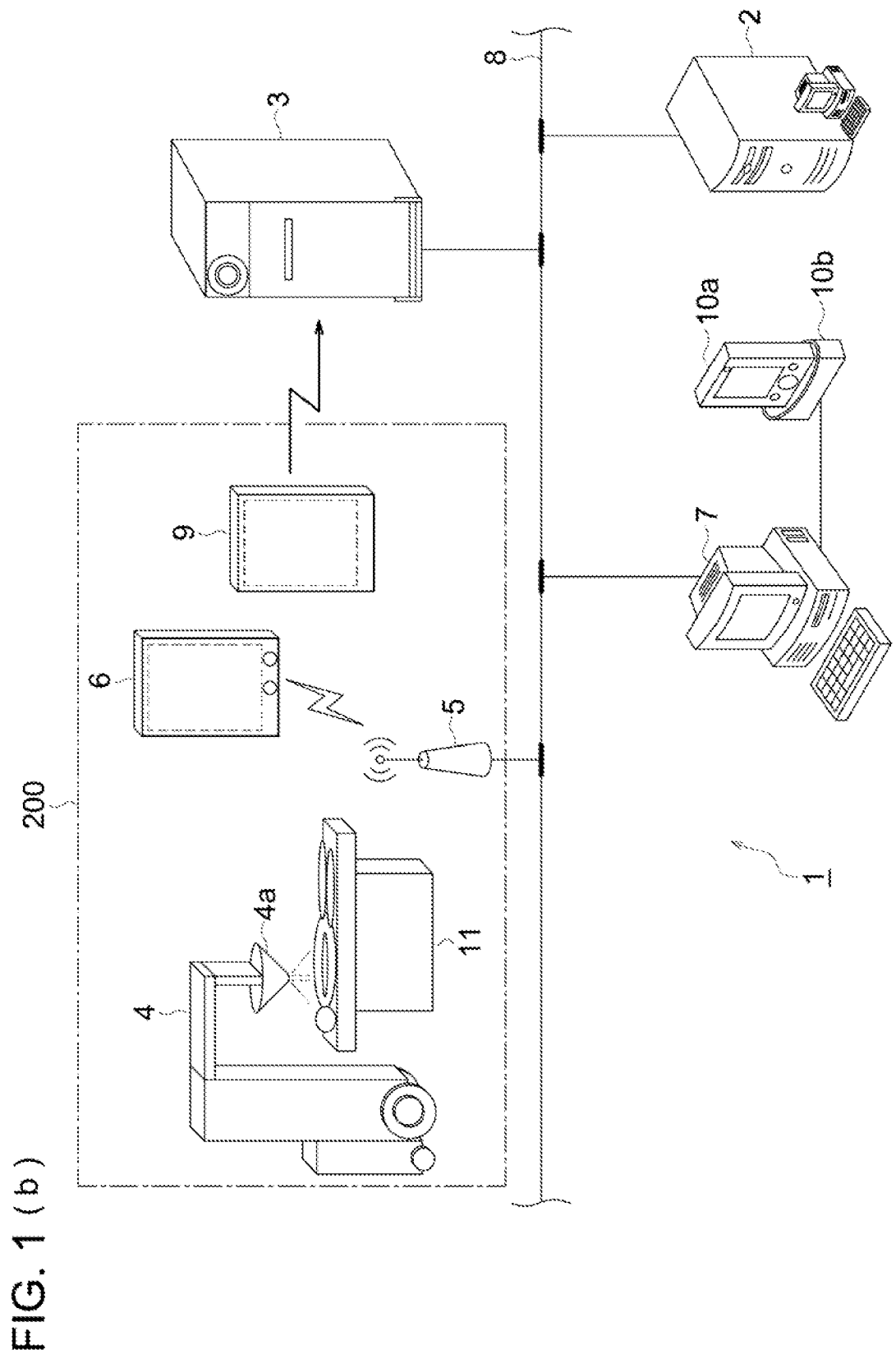

FIG. 1(b) is a schematic diagram showing a fourth embodiment in the RIS (Radiology Information System) 1 of the present invention.

As shown in FIG. 1(b), the RIS 1 as a radiation image radiographing system of the present embodiment includes a management server 2 for managing the radiographing order information for radiographing; a reading apparatus 3 for getting radiation image data by reading the CR cassette 3; a base station 5 for wireless communication on the wireless LAN (Local Area Network); and a console 7 for applying image processing to the generated radiation image data, wherein these components are linked over the network 8. The RIS 1 is also equipped with a portable irradiation apparatus 4 for a doctor's round, and the FPD cassette 6 and CR cassette 9 as radiation image detecting apparatuses. The console 7 is connected with the PDA (Personal Digital Assistance) 10a through a cradle 10b.

Going back to FIG. 1(b), the reading apparatus 3 is a reading apparatus for reading the CR cassette 9. When the CR cassette 9 has been inserted through an inlet (not illustrated), excitation light is applied to the stimulable phosphor plate built in the CR cassette 9. Then the photostimulated luminescence emitted from the stimulable phosphor plate is subjected to photoelectric conversion, and analog-to-digital conversion, whereby radiation image data is obtained.

The irradiation apparatus 4 for a doctor's round can be moved to the ward visited by the doctor. Radiation is applied from the radiation tube 4a, based on the radiographing conditions set on the operation section (not illustrated).

The base station 5 has the function of relaying the wireless communication when the communication is carried out between the FPD cassette 6 and console 7.

The above description also applies to the server 2 and console 7 of the present embodiment.

<Radiation Image Detecting Apparatus>

The CR cassette 9 incorporates a stimulable phosphor panel that stores part of the radiation energy. The radiation dose in conformity to the radiation transmission factor distribution of the inspection object (patient) with respect to the dose applied from the irradiation apparatus 4 for a doctor's round is stored in the stimulable phosphor layer of the built-in stimulable phosphor panel, whereby the radiation image information of the inspection object is recorded. Further, the surface of the casing of the CR cassette 9 is provided with a barcode (not illustrated). As will be described later, this barcode is read by a reading section 107 (barcode reader) of the PDA 10a, whereby cassette ID of the CR cassette 9 is obtained.

The FPD cassette 6 is designed to acquire the radiation image data by detecting the radiation dose in conformity to the radiation transmission factor distribution of the inspection object (patient) with respect to the dose applied from the irradiation apparatus 4 for a doctor's round. It is the aforementioned radiation image detecting apparatus 6 made up of a cassette incorporating the imaging panel which is also referred to as the flat panel detector (FPD).

<PDA>

The PDA 10a is a mobile information terminal apparatus incorporating some of the computer functions. It is capable of receiving the radiographing order information from the console 7 through the cradle 10b and displaying this radiographing order information. For example, a mobile phone or notebook-sized PC (personal computer) can be used as this PDA 10a.

FIG. 2(d) is a block diagram representing the major components of the PDA 10a. As shown in FIG. 2(d), the control system of the PDA 10a is provided with a control section 100, ROM 101, RAM 102, storing section 103, input operation section 104, display section 105, communication section 106, and reading section 107, and these components are connected by a bus 110.

The control section 100 is made up of a CPU, for example. It reads the control program stored in the ROM 101, and loads it in the work area formed in the RAM 102. The components of the PDA 10a are controlled according to the control program.

The ROM 101 is made up of a nonvolatile semiconducting memory, and stores the control program and others executed under the control of the control section 100.

In various forms of processing to be executed and controlled by the control section 100, the RAM 102 forms a work area for temporarily storing the programs which are read out from the ROM 101 and can be executed under the control of the control section 100, as well as the input/output data and parameters.

The storing section 103 stores at least two radiographing order information items sent from the console 7, and the cassette ID of the CR cassette 9 and the cassette ID of the FPD cassette 6 correlated with the radiographing order information.

The input operation section 104 is made up of a plurality of input buttons, for example. When this button is depressed, the input signal conforming to the depression is outputted to the control section 100.

The input operation section 104 is formed of a display section 105, CRT and LCD. Various types of screens are displayed according to the instruction of the display signal outputted from the control section 14 and inputted therein. Of the two or more radiographing order information items stored in the storing section 103, the one radiographing order information item having been inputted from the input operation section 104 is displayed, by way of example.

The reading section 107 is provided with a light emitting member such as a semiconductor laser and LED (Light-Emitting Diode), and an imaging device such as a CCD (Charge Coupled Device). This reading section 107 allows the light emitting member to emit light under the control of the control section 100 so that light is applied to a predetermined surface (the barcode of the CR cassette 9). At the same time, this reading section 107 captures the barcode image by capturing the image in the direction of light emission. Then the image captured by the imaging device is sent to the control section 100.

The communication section 106 exchanges various forms of information with the console 7 in wireless communication mode through the base station 5, using the wireless LAN conforming to the IEEE 802.11 Standard.

The following describes the operation of the RIS 1 with particular emphasis placed on the console 7.

Figure 15:
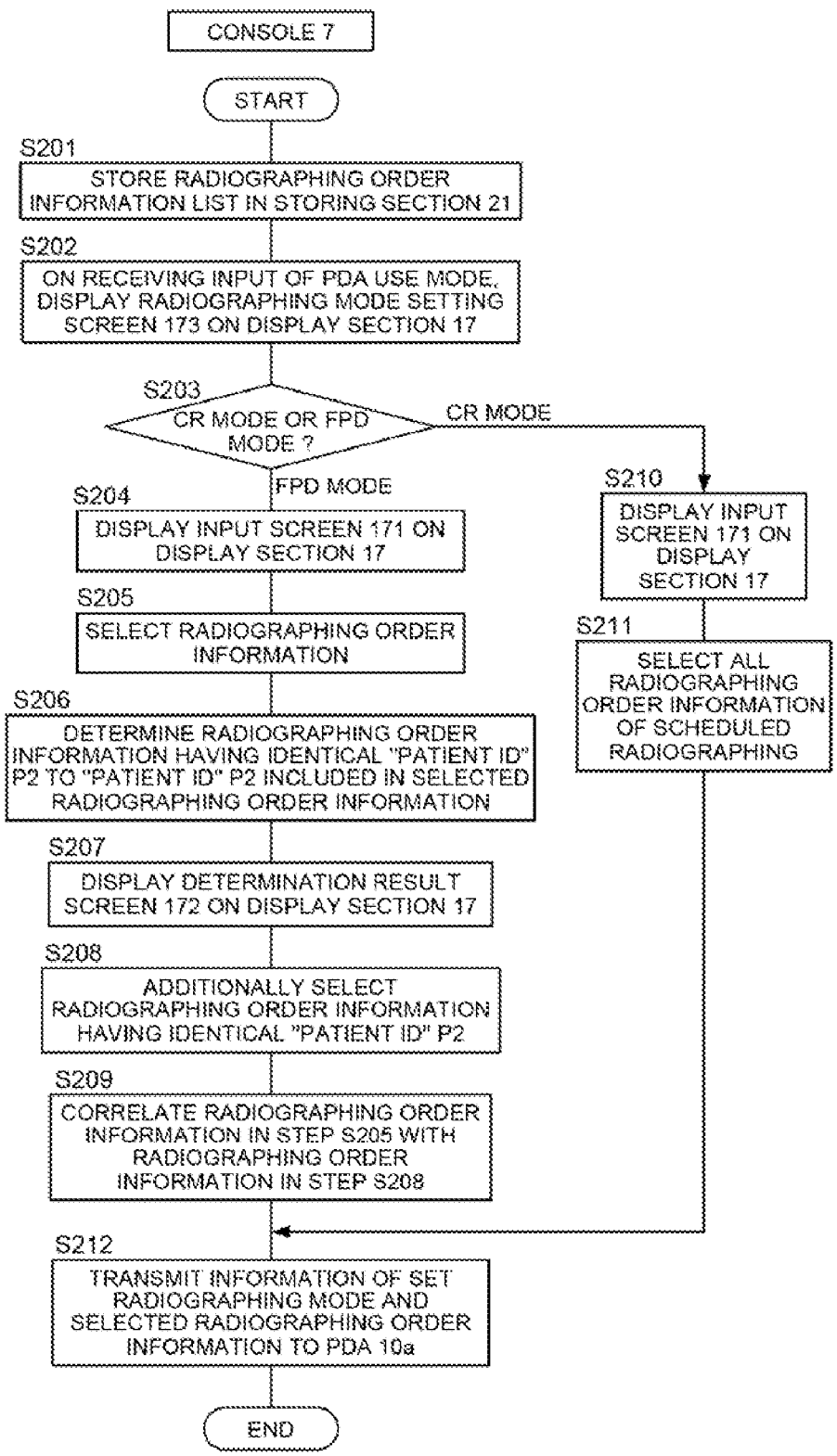
FIG. 15 is a flow chart representing the operation of the console as a fourth embodiment.

FIG. 15 is a flow chart representing the operation of the console 7. Referring to FIG. 15, the following describes the operation of the console 7 when radiographing operation is performed during a doctor's round while carrying a PDA 10a. Assume in this embodiment that plural radiographing order information items on radiographing operation have been inputted in advance by the doctor or personnel in charge of reception. The radiographing order information list of FIG. 5 is stored in the external storing apparatus of the management server 2.

Before starting the radiographing operation, the operator such as the doctor or radiographing technician operates the input operation section 18 of the console 7 to input the information notifying the start of radiographing. Upon receipt of the information notifying the start of radiographing operation from the input operation section 18, the control section 14 of the console 7 receives the radiographing order information list stored in the external storing apparatus of the management server 2, and stores the radiographing order information list in the storing section 21 (Step S201).

A technician operates the input operation section 18 and uses the PDA to input the message notifying the start of radiographing by a doctor's round. Receiving the input from the input operation section 18, the control section 14 displays the radiographing mode input screen 173 on the display section 17 (Step 202).

FIG. 8 is an example showing that the radiographing mode input screen 173 for inputting the radiographing mode is displayed on a display section 17. As shown in FIG. 8, the center of the radiographing mode input screen 173 is equipped with a "CR mode button" 173a and "FPD mode button" 173b. Further, a "Determine button" 173c and "Return button" 173d are also provided below them. The technician operates the input operation section 18, and clicks on the "CR mode button" 173a or "FPD mode button" 173b. If there is no problem, the technician clicks on the "Determine button" 173c.

The CR mode here refers to the mode wherein radiographing operation is performed during a doctor's round, using the CR cassette 9. The FPD mode is the mode wherein radiographing operation is performed during a doctor's round using the FPD cassette 6. The technician selects the CR mode or FPD mode, based on the number of images for radiographing in one round, patient information and radiographing information of the radiographing order information, and positional relationship between the ward of the patient to be visited by the doctor and the site wherein the cassette is placed.

Upon receipt of the input from the input operation section 18, the control section 14 performs the following processing.

<CR Mode>

Upon receipt of the input of the CR mode from the operation input section 18 (CR mode in Step S203), the control section 14 ensures that the input screen 171 for inputting the radiographing order information for this radiographing operation is displayed on the display section 17 (Step S210).

FIG. 6 is an example showing that the input screen 171 for inputting the radiographing order information is displayed on a display section 17.

Upon receipt of the input from the input operation section 18, the control section 14 selects all the inputted radiographing order information from the radiographing order information list stored in the storing section 21 (Step S211). The information on the radiographing mode set in Step 3 and all the radiographing order information selected in the Step 211 are transmitted to the PDA 10a (Step S212). Processing is now completed.

After that, the technician removes the PDA 10a from the cradle 10b, and moves the irradiation apparatus 4 for a round, CR cassettes 9 in the number corresponding to the number of radiographing operations and PDA 10a into the ward 100 of the patient to be radiographed, wherein radiographing operation is performed. To put it more specifically, the technician operates the input operation section 104 of the PDA 10a. Of the radiographing order information items sent from the console 7 and stored in the storing section 21, the one radiographing order information item for the radiographing operation to be started is displayed on the display section 105. Normally, radiographing operation is performed according to the ascending order of "radiographing order ID" P1 of radiographing order information. Thus, in the first place, the radiographing order information of the smallest number of the "radiographing order IDs" P1 is displayed.

The technician selects one CR cassette 9 to be used for radiographing, out of the CR cassettes 9 in the number corresponding to the number of the images of radiographing. The barcode of this CR cassette 9 is read by the reading section 107, whereby the cassette ID of the CR cassette 9 is obtained. Correlation is established between this cassette ID and radiographing order information appearing on the display section 105. This information is stored in the storing section 21 as the correlation information.

According to the radiographing order information appearing on the display section 105, the technician checks the radiographing region of the patient and radiographing direction, and places the one CR cassette 9 having been selected, at the position corresponding to the radiographing region. After that, the technician operates the irradiation apparatus 4 for a round and applies radiation. Then the radiation dose corresponding to the radiation image is accumulated on the CR cassette 9.

The aforementioned radiographing operation is repeated. Upon completion of radiographing operations corresponding to all the radiographing order information stored in the storing section 21, the technician inserts the CR cassettes 9 in the number corresponding to the number of radiographing operations, into the reading apparatus 3, and the radiation image data and cassette ID are obtained for each of the CR cassettes 9. Then the correlation is established between the radiation image data and cassette ID, and this information is then transmitted to the console 7. Further, the PDA 10a is mounted on the cradle 10b, and the information on the correlation between the radiographing order information stored in the storing section 21 of the PDA 10a and cassette ID is sent to the console 7.

In the console 7, correlation is established between the radiation image data sent from the CR cassette 9 and the radiographing order information sent from the PDA 10a, based on the cassette ID of the CR cassette 9. In this case, correlation between the radiation image data and CR cassette and correlation between the radiographing order information and CR cassette are sent to the console 7. This ensures accurate correlation between the radiation image data and radiographing order information.

<FPD Mode>

Upon receipt of the input of the FPD mode from the operation input section 18 (FPD mode in Step S203), the control section 14 ensures that the input screen 171 for inputting the radiographing order information corresponding to this radiographing operation (FIG. 6) is displayed on the display section 17 (Step S204).

While checking the first radiographing order information display area 171a of the display section 17, the technician operates the input operation section 18 and clicks on the item wherein the one radiographing order information item corresponding to this radiographing operation is indicated. Assume in this case that the technician has clicked on the radiographing order information item having a "radiographing order ID" P1 of "001".

Upon receipt of the input from the input operation section 18, the control section 14 selects the one radiographing order information item having a "radiographing order ID" P1 of "001", from the radiographing order information list stored in the storing section 21 (Step S205: selection device for radiographing order information). A decision is made to see whether or not this one selected radiographing order information item and the other radiographing order information item stored in the storing section 21 have a predetermined relationship with each other (Step S206: determining device). To put it more specifically, a step is taken, to determine whether or not the "patient ID" P2 contained in the one selected radiographing order information item and the "patient ID" P2 contained in each of the other radiographing order information item are identical to each other, namely, whether or not the "patient ID" P2 of the other radiographing order information is "100085". Of the other radiographing order information items, the radiographing order information having a "patient ID" P2 of "100085" is displayed on the display section 17 as the determination result screen 172 (Step S207).

FIG. 7 is an example showing that the determination result screen 172 representing the result of determination is displayed on a display section 17. As shown in FIG. 7, the selected radiographing order information display area 172a for displaying the one radiographing order information item selected in Step S205 is arranged on the upper portion of the determination result screen 172. The center of the determination result screen 172 is provided with the second radiographing order information display area 172b for displaying the radiographing order information item having the "patient ID" P2 identical to the selected radiographing order information. Further, the "Determine button" 172c and "Return button" 172d are arranged on the lower portion of the determination result screen 172. As will be described later, permission of additional selection is granted only to the radiographing order information item appearing in the second radiographing order information display area 172b. This corresponds to the permission device of the present invention.

While checking the second radiographing order information display area 172b of the display section 17, the technician operates the input operation section 18 and clicks on a desired radiographing order information item out of the radiographing order information items appearing in the second radiographing order information display area 172b. Normally, it is more efficient in one radiographing flow to select plural radiographing order information items and perform a plurality of radiographing operations together. Thus, it is assumed here that both the radiographing order information items having "radiographing order IDs" P1 of "002" and "003" have been clicked. Upon completion of the input of the radiographing order information, the technician clicks on the "Determine button" 172c.

Upon receipt of the input from the input operation section 18, the control section 14 of the console 7 additionally selects the radiographing order information items having a "patient ID" P2 of "100085", namely, the radiographing order information items having a "radiographing order IDs" P1 of "002" and "003" (Step S208). After correlation has been established between the radiographing order information selected in Step S205 and the radiographing order information selected in Step S208 (Step S209), the information of the radiographing mode set in Step 203 and the radiographing order information selected in Step 209 are sent to the PDA 10a (Step S212). The processing is now completed.

After that, the technician removes the PDA 10a from the cradle 10b, and moves the irradiation apparatus 4 for a round, one FPD cassette 6 and PDA 10a into the ward 100 of the patient to be radiographed, wherein radiographing operation is performed. To put it more specifically, the technician operates the input operation section 104 of the PDA 10a. Correlation is established between three radiographing order information items having been sent from the console 7 and stored in the storing section 21 and the cassette ID of the FPD cassette 6. This information is stored in the storing section 21 as correlation information. In this case, the cassette ID of the FPD cassette 6 for establishing correlation between them can be obtained by using the input operation section 104 to input the cassette ID attached on the surface of the casing of the FPD cassette 6, or by performing infrared communications to get the cassette ID from the FPD cassette 6.

The technician operates the input operation section 104 of the PDA 10a, and ensures that, of the three radiographing order information items stored in the storing section 103, the one radiographing order information item to be radiographed is displayed on the display section 105. Normally, radiographing operation is performed according to the ascending order of "radiographing order ID" P1 of the radiographing order information item. Thus, radiographing order information having a "radiographing order ID" P1 of the lowest number is displayed first.

After checking the radiographing region of the patient and the direction of radiographing according to the radiographing order information displayed on the display section 105, the technician installs the FPD cassette 6 at a position corresponding to the radiographing region. Then the technician operates the irradiation apparatus 4 for a round so that radiation is applied. Then the radiation image data is generated by the FPD cassette 6 and is stored in the image storing section 66.

Upon completion of the radiographing operation according to the three radiographing order information items by repeating the aforementioned radiographing operation, the technician depresses the transmission button (not illustrated) provided on the FPD cassette 6, and the radiation image data for three radiographing operations stored in the image storing section 66 is sent to the console 7 through the base station 5 in the order in which radiographing has been performed (in the order of radiographing). In this case, radiation image data together with the cassette ID of the FPD cassette 6 attached thereto is transmitted. After that, the PDA 10a is mounted on the cradle 10b, and the radiographing order information stored in the storing section 21 of the PDA 10a and the correlation information related to the cassette ID are transmitted to the console 7.

In the console 7, correlation is established between the radiation image data for three radiographing operations transmitted from the FPD cassette 6 and the three radiographing order information items transmitted from the PDA 10a. It should be noted that this correlation is carried out according to the sequential order of transmission (order of radiographing operation) in which radiation image data has been sent from the FPD cassette 6, and according to the ascending order of "radiographing order ID" P1. As described above, in the normal radiographing mode, radiographing operation is performed according to the ascending order of "radiographing order ID" P1. At the same time, radiation image data is stored in the image storing section 66 of the FPD cassette 9 in this order of radiographing. Thus, when the correlation is established in the console 7 based on the sequential order of radiographing (order of transmission) of the radiation image data and the "radiographing order ID" P1 according to the ascending order, accurate correlation can be ensured automatically.

For example, if the radiographing operation cannot be performed (or has not been performed) according to the ascending order of "radiographing order ID" P1 for the reasons of the technician or patient, the ascending order of "radiographing order ID" P1 is different from the order of radiographing. Accordingly, if the aforementioned method is used to establish correlation between the radiation image data and radiographing order information, a correlation error will occur. In this case, if the three radiographing order information items contain the radiographing order information whose radiographing region is identical (or similar), radiographing operation is performed based on this radiographing order information and the generated radiation image data will be identical (or similar). In this case, the technician cannot identify radiation image data. This makes it difficult to take notice of incorrect correlation between the radiation image data and radiographing order information.

In the FPD mode, the radiographing order information to be sent to the PDA 10a according to the procedure described in the aforementioned Step 206 through Step 208, only the radiographing order information of one patient can be transmitted. Normally, when the same patient is radiographed several times, overlapped radiographing of the same or similar region in one radiographing flow rarely occurs. The radiation image data generated in conformity to the radiographing order information of one patient can be easily identified by the technician. Thus, the technician displays the radiation image data and radiographing order information on the display section 17 of the console 7. If there is an incorrect correlation, the technician is allowed to get a correct correlation by operating the input operation section 18.

As described above, in the FPD mode of the present embodiment, a plurality of radiographing operations are performed using one FPD cassette 6, and radiation image data corresponding to plural radiographing operations is generated. Before selecting plural radiographing order information items corresponding to radiation image data for plural radiographing operations, if one radiographing order information item has been selected, a step is taken to determine whether or not the "patient ID" P2 of the one radiographing order information item and "patient ID" P2 of the other radiographing order information item are identical to each other. Permission of additional selection is granted only to the other radiographing order information item whose "patient ID" P2 is identical. As described above, normally, when one patient is radiographed several times, overlapped radiographing of the identical or similar region in one radiographing flow rarely occurs.

Thus, even if one patient is radiographed several times by one FPD cassette 6 and the generated radiation image data corresponding to plural radiographing operations is stored simultaneously, the technician is allowed to identify the correlation between radiation image data and radiographing order information, when the radiation image data corresponding to plural radiographing operations is displayed on the console 7. Accordingly, even if there is an incorrect correlation between the radiation image data and radiographing order information, the technician easily takes note of the error to take action to get correct correlation. This arrangement prevents confusion of radiation image data, and hence minimizes the possibility of generating an medical error.

Based on the one selected radiographing order information item, the control section 14 of the console 7 determines the radiographing order information to which the permission of additional selection can be granted. Thus, when the radiographing order information is additionally selected, there is no need for the doctor to make a decision, with the result that work efficiency is enhanced.

The determination result screen 172 showing the determination result is displayed on the display section 17. Based on this determination result, the radiographing order information to which the permission of additional selection has been granted is inputted. This arrangement provides a screen, understood at a glance, of the radiographing order information to which the permission of additional selection can be granted, and hence minimizes the possible omission in the selection of the radiographing order information by the technician.

The CR mode and FPD mode can be selected so that the optimum a radiographing mode can be selected in response to a particular requirement, with the result that radiographing work efficiency is enhanced.

In the aforementioned embodiment, the radiographing order information item having the "patient ID" P2 identical to that of the one selected radiographing order information item is set as the radiographing order information item having a predetermined relationship with the one selected radiographing order information item. It goes without saying that the present invention is not restricted thereto. For example, the radiographing order information item having the "radiographing region" P7 different from the "radiographing region" P7 contained in the one selected radiographing order information item, or the radiographing order information having the "radiographing region" P7 and "radiographing direction" P8 wherein at least one of the "radiographing region" P7 and "radiographing direction" P8 is different from ones of the one selected radiographing order information item can be set as the radiographing order information item having a predetermined relationship with the one selected radiographing order information item.

Even if data of plural radiation images obtained by radiographing different patients are stored simultaneously in one FPD cassette 6, this setting allows the technician to identify correlation between radiation image data and radiographing order information. This arrangement permits radiographing operation to be performed across a plurality of patients in one radiographing flow, with the result that radiographing efficiency is farther improved. In the meantime, for example, when radiographing the L (left) and R (right) in the vertical direction (also called "CC") of the breast region, the radiation image data cannot be identified, even if there is a difference in the "radiographing direction" P8 between L and R. This may cause confusion of the radiation image data. Therefore, when radiation image data cannot be identified as in the case of the CC-L and CC-R of the breast region, simultaneous selection is prohibited. As described above, having a predetermined relationship in the present invention permits the possibility of adequate setting in response to the individual work form, to the extent that the technician can identify the radiation image data.

In the aforementioned description, when radiographing order information is additionally selected, it is selected in response to the input by the technician through the input operation section 18. However, as described above, in one radiographing flow, radiographing efficiency is enhanced when plural radiographing order information items are selected, and a plurality of radiographing operations are performed together. Thus, it is also possible to make such arrangements that all the radiographing order information items to which permission of additional selection is granted are automatically selected. This arrangement eliminates the need of radiographing order information being additionally selected by the doctor. Thus, the work efficiency is enhanced, and all the radiographing order information item that can be radiographed are automatically selected in one radiographing flow, with the result that there is no possibility of omission in the selection of radiographing order information items.

In one radiographing operation during a doctor's round, radiographing is carried out in either the CR mode or FPD mode, as described above. However, radiographing can be performed using a combination of these modes. For example, the FPD mode is set on the console 7, and the one radiographing order information item and the radiographing order information item having a predetermined relationship with this radiographing order information item are transmitted to the PDA 10a. Then the CR mode is set. Of the radiographing order information items except for the radiographing order information item having been transmitted to the PDA 10a in the FPD mode, all the desired radiographing order information items are transmitted to the PDA 10a. After the Irradiation apparatus 4 for a round, one FPD cassette 6, CR cassettes 9 in the number corresponding to the number of radiographing operations in the CR mode and PDA 10a have been carried into the ward 100, the radiographing operation is performed by switching between the CR mode and FPD mode by the PDA 10a.

As described above, radiographing can be performed successfully using the CR cassette 9 in the case of the radiographing order information wherein radiation image data cannot be identified if radiographing is performed using a FPD cassette 6, as utilizing a combination between the CR mode and FPD mode. This arrangement allows radiographing operations to be performed together in one radiographing operation flow, while minimizing the number of the cassettes to be carried (used) by the technician, with the result that the radiographing work efficiency is further enhanced.

In the aforementioned description, when correlation is established between the radiographing order information and radiation image data by the console 7, radiation image data is transmitted from the FPD cassette 6 through the base station 5, and the radiographing order information is transmitted from the PDA 10a through the cradle 10b. In other words, these pieces of data are transmitted separately to the console 7. However, without the present invention being restricted thereto, it is also possible to make such arrangements, for example, that, before radiographing, radiographing order information is transmitted from the PDA 10a to the FPD cassette 6 so that it is stored in the FPD cassette 6. When the radiation image data is to be sent from the FPD cassette 6 to the console 7, the radiographing order information is also sent together.

According to the present invention, when the one radiographing order information item has been selected, the permission of additional selection is granted only to the radiographing order information having a predetermined relationship with the one radiographing order information item. This arrangement allows the technician to identify (distinguish) the radiation image data and to take notice of any error easily that may be present in the correlation established between the radiation image data and radiographing order information, hence to take a remedial step to get correct correlation between the radiation image data and radiographing order information, with the result that possible confusion of radiation image data is prevented and generation of a medical error is minimized.

What is claimed is:

1. A radiation image radiographing system comprising:
   a control apparatus for storing a plurality of radiographing order information items related to radiographing;
   a radiation image detecting apparatus which is a flat panel detector capable of storing image data of a plurality of images and, when radiographing is performed based on two or more radiographing order information items selected among the plurality of radiographing order information items, can generate and store radiation image data corresponding to the two or more radiographing order information items, the control apparatus and the radiation image apparatus being connected communicably;
   a selection device which, for selecting the two or more radiographing order information items, selects at least one radiographing order information item among the plurality of radiographing order information items stored in the control apparatus;
   a determining device for determining whether or not a patient of one radiographing order information item selected by the selection device and a patient of another radiographing order information item different from the one radiographing order information item are identical; and
   a permission device for permitting only the another radiographing order information item to be additionally selected, the patient of which has been determined to be identical to the patient of the one radiographing order information item by the determining device.

2. The radiation image radiographing system of claim 1, comprising:
   a management apparatus for transmitting, to the radiation image detecting apparatus, the two or more radiographing order information items including the one radiographing order information item selected by the selection device, the radiation image detecting apparatus and the management apparatus being connected communicably, the management apparatus comprising:
      a receiving section for receiving the one radiographing order information item transmitted from the first transmitting section; and
      a second transmitting section for transmitting, to the radiation image detecting apparatus, the one radiographing order information item and the another radiographing order information item which is permitted by the permission device to be additionally selected, and
   a first transmitting section for transmitting, to the management apparatus, the one radiographing order information item selected by the selection device,
   wherein the radiation image radiographing system, when radiographing is performed based on the two or more radiographing order information items transmitted from the management apparatus, can generate and store radiation image data corresponding to the two or more radiographing order information items by using the radiation image detecting apparatus.

3. The radiation image radiographing system of claim 2, wherein when the receiving section receives the one radiographing order information item, the determining device automatically determines whether or not the patient of the one radiographing order information item and the patient of each of the plurality of radiographing order information items stored in advance are identical.

4. The radiation image radiographing system of claim 1, further comprising;
   a mobile information terminal apparatus communicably connected for storing two or more radiographing order information items selected among the plurality of radiographing order information items.

5. The radiation image radiographing system of claim 1, further comprising;
   a display section for displaying a screen of a determination result of the determining device; and
   an input operation section for inputting a radiographing order information item which is permitted by the permission device to be additionally selected based on the determination result displayed on the display section.

6. The radiation image radiographing system of claim 1, wherein a radiographing order information item which is permitted to be additionally selected by the permission device is additionally selected automatically.

7. A control apparatus connected communicably with a radiation image detecting apparatus which is a flat panel detector capable of storing image data of a plurality of images and, when radiographing is performed based on two or more radiographing order information items selected among a plurality of radiographing order information items, can generate and store radiation image data corresponding to the two or more radiographing order information items; the control apparatus comprising:
   a control storing section for storing the plurality of radiographing order information items;
   a selected device which, for selecting the two or more radiographing order information items, selects at least one radiographing order information item among the plurality of radiographing order information items stored in the control storing section;
   a determining device for determining whether or not a patient of one radiographing order information item selected by the selection device, and a patient of another radiographing order information item different from the one radiographing order information item are identical; and
   a permission device for permitting only the another radiographing order information item to be additionally selected, the patient of which has been determined to be identical to the patient of the one radiographing order information item by the determining device.

8. A radiation image detecting apparatus which is a flat panel detector capable of storing image data of a plurality of images and is communicably connected with a control apparatus which stores a plurality of radiographing order information items, the radiation image detecting apparatus comprising:
- a receiving section for receiving two or more radiographing order information items among the plurality of radiographing order information items;
- a radiographing order information storing section for storing one radiographing order information item received by the receiving section, as a selected radiographing order information item;
- a determining device for determining whether or not a patient of the selected radiographing order information item stored in the radiographing order information storing section and a patient of another radiographing order information item different from the selected radiographing order information item are identical;
- a permission device for permitting only the another radiographing order information item to be additionally selected, the patient of which has been determined to be identical to the patient of the one radiographing order information item by the determining device;
- an image data generating section which, by detecting a radiation having passed through a subject, generates radiation image data corresponding respectively to the selected radiographing order information item and the another radiographing order information item which is permitted by the permission device to be additional selected; and
- an image storing section for storing data of a plurality of radiation images generated by the image data generating section.

9. A management apparatus communicably connected with a control apparatus which selects at least one radiographing order information item related to radiographing and a radiation image detecting apparatus which is a flat panel detector capable of storing image data of a plurality of images and receives two or more radiographing order information items including the at least one radiographing order information item, and is capable of generating and storing radiation image data corresponding to the two or more radiographing order information items, the management apparatus comprising:
- a receiving section which, for selecting the two or more radiographing order information items, receives the one radiographing order information item selected by the control apparatus;
- a determining device for determining whether or not a patient of the one radiographing order information item received by the receiving section and a patient of another radiographing order information item different from the one radiographing order information item are identical;
- a permission device for permitting only the another radiographing order information item to be additionally selected, the patient of which has been determined to be identical to the patient of the one radiographing order information item by the determining device; and
- a radiographing order information transmitting section for transmitting, to the radiation image detecting apparatus, the one radiographing order information item and the another radiographing order information item which is permitted by the permission device to be additionally selected.

10. A radiation image radiographing system, comprising:
a control apparatus for storing a plurality of radiographing order information items related to radiographing;
- a radiation image detecting apparatus which is a flat panel detector capable of storing image data of a plurality of images and, when radiographing is performed based on two or more radiographing order information items selected among the plurality of radiographing order information items, can generate and store radiation image data corresponding to the two or more radiographing order information items, the control apparatus and the radiation image detecting apparatus being connected communicably;
- a selection device which, for selecting the two or more radiographing order information items, selects at least one radiographing order information item among the plurality of radiographing order information items stored in the control apparatus;
- a determining device for determining whether or not a radiographing region and a radiographing direction of one radiographing order information item selected by the selection device and a radiographing region and a radiographing direction of another radiographing order information item different from the one radiographing order information item are different; and
- a permission device for permitting only the another radiographing order information item to be additionally selected, at least one of the radiographing region and the radiographing direction of which has been determined to be different from the radiographing region and the radiographing direction of the one radiographing order information item by the determining device.

11. The radiation image radiographing system of claim 10, further comprising:
- a management apparatus for transmitting, to the radiation image detecting apparatus, the two or more radiographing order information items including the one radiographing order information item selected by the selection device, the radiation image detecting apparatus and the management apparatus being connected communicably, the management apparatus comprising:
  - a receiving section for receiving the one radiographing order information item transmitted from the first transmitting section; and
  - a second transmitting section for transmitting, to the radiation image detecting apparatus, the one radiographing order information item and the another radiographing order information item which is permitted by the permission device to be additionally selected, and
- a first transmitting section for transmitting, to the management apparatus, the one radiographing order information item selected by the selection device,
- wherein the radiation image radiographing system, when radiographing is performed based on the two or more radiographing order information items transmitted from the management apparatus, can generate and store radiation image data corresponding to the two or more radiographing order information items by using the radiation image detecting apparatus.

12. The radiation image radiographing system of claim 11, wherein when the receiving section receives the one radiographing order information item, the determining device automatically determines whether or not a radiographing region and a radiographing direction of the one radiographing order information item and a radiographing region and a radiographing direction of each of the plurality of radiographing order information items stored in advance are different.

13. The radiation image radiographing system of claim 10, further comprising:
- a mobile information terminal apparatus communicably connected for storing two or more radiographing order information items selected among the plurality of radiographing order information items.

14. The radiation image radiographing system of claim 10, further comprising:
- a display section for displaying a screen of a determination result of the determining device; and
- an input operation section for inputting a radiographing order information item which is permitted by the permission device to be additionally selected based on the determination result displayed on the display section.

15. The radiation image radiographing system of claim 10, wherein a radiographing order information item which is permitted to be additionally selected by the permission device is additionally selected automatically.

16. A control apparatus connected communicably with a radiation image detecting apparatus which is a flat panel detector capable of storing image data of a plurality of images and, when radiographing is performed based on two or more radiographing order information items selected among a plurality of radiographing order information items, can generate and store radiation image data corresponding to the two or more radiographing order information items, the control apparatus comprising:
- a control storing section for storing the plurality of radiographing order information items;
- a selection device which, for selecting the two or more radiographing order information items, selects at least one radiographing order information item among the plurality of radiographing order information items stored in the control storing section;
- a determining device for determining whether or not a radiographing region and a radiographing direction of one radiographing order information item selected by the selection device, and a radiographing region and a radiographing direction of another radiographing order information item different from the one radiographing order information item are different; and
- a permission device for permitting only the another radiographing order information item to be additionally selected, at least one of the radiographing region and the radiographing direction of which has been determined to be different from the radiographing region and the radiographing direction of the one radiographing order information item by the determining device.

17. A radiation image detecting apparatus which is a flat panel detector capable of storing image data of a plurality of images and is communicably connected with a control apparatus which stores a plurality of radiographing order information items, the radiation image detecting apparatus comprising:
- a receiving section for receiving two or more radiographing order information items among the plurality of radiographing order information items;
- a radiographing order information storing section for storing one radiographing order information item received by the receiving section, as a selected radiographing order information item;
- a determining device for determining whether or not a radiographing region and a radiographing direction of the selected radiographing order information stored in the radiographing order information storing section and a radiographing region and a radiographing direction of another radiographing order information item different from the selected radiographing order information item are different;
- a permission device for permitting only the another radiographing order information item to be additionally selected, at least one of the radiographing region and the radiographing direction of which has been determined to be different from the radiographing region and the radiographing direction of the one radiographing order information item by the determining device;
- an image device generating section which, by detecting a radiation having passed through a subject, generates radiation image data corresponding relatively to the selected radiographing order information item and the another radiographing order information item which is permitted by the permission device to be additionally selected; and
- an image storing section for storing data of a plurality of radiation images generated by the image data generating section.

18. A management apparatus communicably connected with a control apparatus which selects at least one radiographing order information item related to radiographing and a radiation image detecting apparatus which is a flat panel detector capable of storing image data of a plurality of images and receives two or more radiographing order information items including the at least one radiographing order information item, and is capable of generating and storing radiation image data corresponding to the two or more radiographing order information items, the management apparatus comprising:
- a receiving section which, for selecting the two or more radiographing order information items, receives the one radiographing order information item selected by the control apparatus;
- a determining device for determining whether or not a radiographing region and a radiographing direction of the one radiographing order information item received by the receiving section and a radiographing region and a radiographing direction of another radiographing order information item different from the one radiographing order information item are different;
- a permission device for permitting only the another radiographing order information item to be additionally selected, at least one of the radiographing region and the radiographing direction of which has been determined to be different from the radiographing region and the radiographing direction of the one radiographing order information item by the determining device; and
- a radiographing order information transmitting section for transmitting, to the radiation image detecting apparatus, the one radiographing order information item and the another radiographing order information item which is permitted by the permission device to be additionally selected.

* * * * *